US012617871B2

(12) United States Patent
Yin et al.

(10) Patent No.: US 12,617,871 B2
(45) Date of Patent: May 5, 2026

(54) ANTI-CD47/ANTI-TIGIT BISPECIFIC ANTIBODY, PREPARATION METHOD THEREFOR AND APPLICATION THEREOF

(71) Applicant: Nanjing GenScript Biotech Co., Ltd., Nanjing (CN)

(72) Inventors: Liusong Yin, Nanjing (CN); Zhongdao Li, Nanjing (CN); Tielin Zhou, Singapore (SG); Zhuo Fang, Nanjing (CN)

(73) Assignee: Nanjing GenScript Biotech Co., Ltd., Nanjing (CN)

( * ) Notice: Subject to any disclaimer, the term of this patent is extended or adjusted under 35 U.S.C. 154(b) by 1178 days.

(21) Appl. No.: 17/618,609

(22) PCT Filed: Jun. 24, 2020

(86) PCT No.: PCT/CN2020/097924
§ 371 (c)(1),
(2) Date: Dec. 13, 2021

(87) PCT Pub. No.: WO2020/259535
PCT Pub. Date: Dec. 30, 2020

(65) Prior Publication Data
US 2022/0267475 A1 Aug. 25, 2022

(30) Foreign Application Priority Data
Jun. 25, 2019 (CN) .......................... 201910554742.1

(51) Int. Cl.
*C07K 16/46* (2006.01)
*C07K 16/28* (2006.01)

(52) U.S. Cl.
CPC ........ *C07K 16/468* (2013.01); *C07K 16/2803* (2013.01); *C07K 16/2809* (2013.01); *C07K 2317/31* (2013.01); *C07K 2317/53* (2013.01); *C07K 2317/565* (2013.01); *C07K 2317/569* (2013.01); *C07K 2317/76* (2013.01); *C07K 2317/92* (2013.01)

(58) Field of Classification Search
CPC .............. C07K 16/468; C07K 2317/31; C07K 2317/569; C07K 2319/00; C07K 2317/565
See application file for complete search history.

(56) References Cited

U.S. PATENT DOCUMENTS

| | | | |
|---|---|---|---|
| 11,905,327 B2 * | 2/2024 | Zhang | C07K 16/2818 |
| 2020/0399367 A1 * | 12/2020 | Gong | A61P 35/00 |

FOREIGN PATENT DOCUMENTS

| | | | | |
|---|---|---|---|---|
| CN | 110352200 A | 10/2019 | | |
| WO | WO-2018014855 A1 * | 1/2018 | .............. | A61P 29/00 |
| WO | WO-2018224951 A2 * | 12/2018 | ........ | C07K 16/1027 |
| WO | WO 2019/129221 A1 | 7/2019 | | |
| WO | WO 2019/144895 A1 | 8/2019 | | |
| WO | WO 2019/154415 A1 | 8/2019 | | |

OTHER PUBLICATIONS

Paul, Fundamental Immunology, 3rd Edition, 1993, pp. 292-295, (Year: 1993).*
Almagro & Fransson, Frontiers in Bioscience 2008; 13:1619-33 (Year: 2008).*
Rudikoff et al (Proc. Natl. Acad. Sci. USA 1982 Vol. 79: p. 1979) (Year: 1982).*
Pascalis et al (The Journal of Immunology (2002) 169, 3076-3084) (Year: 2002).*
Casset et al. (2003) BBRC 307, 198-205 (Year: 2003).*
D'Angelo et al, Frontiers in Immunology vol. 9 p. 1 (2018) (Year: 2018).*
Brown et al (J. Immunol. May 1996; 156(9):3285-3291 at p. 3290 (Year: 1996).*
Vajdos et al (J. Mol. Biol. Jul 5, 2002;320(2); 415-428 (Year: 2002).*
Extended European Search Report for EP 20832938.3, issued by the European Patent Office, mailed on Jul. 14, 2023 (8 pages).
Zhang et al., "Blockade of the checkpoint receptor TIGIT prevents NK cell exhaustion and elicits potent anti-tumor immunity," *Nature Immunology*, vol. 19:723-732, 2018.
Liu et al., "Anti-CD47 Antibody as a Targeted Therapeutic Agent for Human Lung Cancer and Cancer Stem Cells," *Frontiers in Immunology*, vol. 8, Article 404, Apr. 21, 2017, (17 pages).
International Search Report and Written Opinion mailed on Oct. 9, 2020 for International Application No. PCT/CN2020/097924 (9 pages).
English translation of International Search Report mailed on Oct. 9, 2020 for International Application No. PCT/CN2020/097924 (3 pages).

* cited by examiner

*Primary Examiner* — Fereydoun G Sajjadi
(74) *Attorney, Agent, or Firm* — Yong Chen; Lin Sun-Hoffman; Liu Chen & Hoffman LLP

(57) ABSTRACT

Anti-CD47/anti-TIGIT bispecific antibody, a preparation method thereof and application thereof. The bispecific antibody comprises: (a) a first antigen binding part, comprising heavy chain variable region ($V_H$) and light chain variable region ($V_L$), $V_H$ and $V_L$ forming an antigen binding site that specifically binds to CD47; and (b) a second antigen binding part, comprising a single domain antibody (sdAb) that specifically binds to TIGIT, wherein the first antigen binding part and the second antigen binding part are fused with each other. The bispecific antibody can block two modes of tumor immune escape at the same time, thus having a good effect in tumor immunotherapy.

6 Claims, 2 Drawing Sheets
Specification includes a Sequence Listing.

| | TIGIT-E-LC | TIGIT-G9-LC | TIGIT-E-HC | TIGIT-G9-HC | TIGIT-E-HN | TIGIT-G9-HN |
|---|---|---|---|---|---|---|
| EC50 | 0.3341 | 0.6576 | 0.5204 | 0.4288 | 0.1318 | 0.1684 |

| | TIGIT-E-LN | TIGIT-G9-LN | sdab-TIGIT-IgG4PE | Anti-CD47 antibody | Human IgG |
|---|---|---|---|---|---|
| EC50 | 0.07568 | 0.1551 | 0.4599 | ~ 0.4431 | ~ 0.01499 |

| | TIGIT-G9-HC | TIGIT-E-HN | TIGIT-G9-HN | TIGIT-E-LC | TIGIT-E-LN |
|---|---|---|---|---|---|
| EC50 | 0.6860 | 0.6498 | 0.8523 | 0.6526 | 0.3700 |

| | TIGIT-G9-LN | sdab-TIGIT-IgG4PE | Anti-CD47 antibody | Human IgG |
|---|---|---|---|---|
| EC50 | 1.042 | ~0.06947 | 0.008430 | ~0.0009918 |

SEQUENCE LISTING

```
<160> NUMBER OF SEQ ID NOS: 41

<210> SEQ ID NO 1
<211> LENGTH: 57
<212> TYPE: DNA
<213> ORGANISM: Artificial Sequence
<220> FEATURE:
<223> OTHER INFORMATION: DNA sequence of secretion signal peptide

<400> SEQUENCE: 1
atgggctggt cctgcatcat cctgttcctg gtggctaccg ccaccggcgt gcactcc          57

<210> SEQ ID NO 2
<211> LENGTH: 19
<212> TYPE: PRT
<213> ORGANISM: Artificial Sequence
<220> FEATURE:
<223> OTHER INFORMATION: Amino acid sequence of secretion signal peptide

<400> SEQUENCE: 2

Met Gly Trp Ser Cys Ile Ile Leu Phe Leu Val Ala Thr Ala Thr Gly
1               5                   10                  15

Val His Ser

<210> SEQ ID NO 3
<211> LENGTH: 1332
<212> TYPE: DNA
<213> ORGANISM: Artificial Sequence
```

```
<220> FEATURE:
<223> OTHER INFORMATION: DNA sequence of a heavy chain of anti-CD47
      antibody

<400> SEQUENCE: 3
gaggtgcagc tggtgcagtc cggagctgag gtgaagaagc caggatccag cgtgaaggtg      60
agctgcaagg ctagcggcta ctctttcacc caccattgga tccactgggt gaggcaggct     120
cctggacagg gactggagtg gatgggcatg atcgacgctt ccgatagcga gacaagactg     180
tctcagaagt ttaaggaccg cgtgaccatc acagccgata agtctacctc cacagcttac     240
atggagctgt cttccctgag atccgaggac accgccgtgt actattgtgc taggctgggc     300
cggtactatt tcgattattg gggccagggc accacagtga cagtgagctc tgccagcaca     360
aagggccctt ccgtgttccc actggctccc tgctccagaa gcacatctga gtccaccgcc     420
gctctgggct gtctggtgaa ggactacttc cctgagccag tgaccgtgtc ctggaacagc     480
ggcgccctga catctggcgt gcacaccttt ccagctgtgc tgcagtccag cggcctgtac     540
tccctgtctt ccgtggtgac agtgcccagc tcttccctgg gcaccaagac atatacctgc     600
aacgtggacc ataagccttc caataccaag gtggataaga gggtggagag caagtacgga     660
ccaccttgcc caccatgtcc agctcctgag tttgaggggg accatccgt gttcctgttt      720 cctccaaagc ctaaggacac cctgatgatc agccggacac ctgaggtgac ctgcgtggtg     780
gtggacgtgt ctcaggagga tccagaggtg cagttcaact ggtacgtgga tggcgtggag     840
gtgcacaatg ctaagaccaa gccaagagag gagcagttta attccacata ccgcgtggtg     900
agcgtgctga ccgtgctgca tcaggattgg ctgaacggca aggagtataa gtgcaaggtg     960
tccaataagg gcctgcccag ctctatcgag aagacaatca gcaaggctaa gggacagcct    1020
agggagccac aggtgtacac cctgccccct tctcaggagg agatgacaaa gaaccaggtg    1080
tccctgacct gtctggtgaa gggcttctat ccaagcgaca tcgctgtgga gtgggagtct    1140
aatggccagc ccgagaacaa ttacaagacc acaccacccg tgctggactc tgatggctcc    1200
ttctttctgt attctaggct gacagtggat aagtcccggt ggcaggaggg caacgtgttt    1260
agctgctctg tgatgcacga ggccctgcac aatcattata cccagaagtc cctgagcctg    1320
tctctgggca ag                                                       1332

<210> SEQ ID NO 4
<211> LENGTH: 444
<212> TYPE: PRT
<213> ORGANISM: Artificial Sequence
<220> FEATURE:
<223> OTHER INFORMATION: Amino acid sequence of a heavy chain of
      anti-CD47 antibody (H0)

<400> SEQUENCE: 4

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr His His
            20                  25                  30

Trp Ile His Trp Val Arg Gln Ala Pro Gly Gln Gly Leu Glu Trp Met
        35                  40                  45

Gly Met Ile Asp Ala Ser Asp Ser Glu Thr Arg Leu Ser Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
```

-continued

```
                         85                    90                    95
Ala Arg Leu Gly Arg Tyr Tyr Phe Asp Tyr Trp Gly Gln Gly Thr Thr
            100                   105                   110
Val Thr Val Ser Ser Ala Ser Thr Lys Gly Pro Ser Val Phe Pro Leu
            115                   120                   125
Ala Pro Cys Ser Arg Ser Thr Ser Glu Ser Thr Ala Ala Leu Gly Cys
    130                   135                   140
Leu Val Lys Asp Tyr Phe Pro Glu Pro Val Thr Val Ser Trp Asn Ser
145                   150                   155                   160
Gly Ala Leu Thr Ser Gly Val His Thr Phe Pro Ala Val Leu Gln Ser
                165                   170                   175
Ser Gly Leu Tyr Ser Leu Ser Ser Val Val Thr Val Pro Ser Ser Ser
                180                   185                   190
Leu Gly Thr Lys Thr Tyr Thr Cys Asn Val Asp His Lys Pro Ser Asn
                195                   200                   205
Thr Lys Val Asp Lys Arg Val Glu Ser Lys Tyr Gly Pro Pro Cys Pro
    210                   215                   220
Pro Cys Pro Ala Pro Glu Phe Glu Gly Gly Pro Ser Val Phe Leu Phe
225                   230                   235                   240
Pro Pro Lys Pro Lys Asp Thr Leu Met Ile Ser Arg Thr Pro Glu Val
                245                   250                   255
Thr Cys Val Val Val Asp Val Ser Gln Glu Asp Pro Glu Val Gln Phe
                260                   265                   270
Asn Trp Tyr Val Asp Gly Val Glu Val His Asn Ala Lys Thr Lys Pro
                275                   280                   285
Arg Glu Glu Gln Phe Asn Ser Thr Tyr Arg Val Val Ser Val Leu Thr
    290                   295                   300
Val Leu His Gln Asp Trp Leu Asn Gly Lys Glu Tyr Lys Cys Lys Val
305                   310                   315                   320
Ser Asn Lys Gly Leu Pro Ser Ser Ile Glu Lys Thr Ile Ser Lys Ala
                325                   330                   335
Lys Gly Gln Pro Arg Glu Pro Gln Val Tyr Thr Leu Pro Pro Ser Gln
                340                   345                   350
Glu Glu Met Thr Lys Asn Gln Val Ser Leu Thr Cys Leu Val Lys Gly
                355                   360                   365
Phe Tyr Pro Ser Asp Ile Ala Val Glu Trp Glu Ser Asn Gly Gln Pro
    370                   375                   380
Glu Asn Asn Tyr Lys Thr Thr Pro Pro Val Leu Asp Ser Asp Gly Ser
385                   390                   395                   400
Phe Phe Leu Tyr Ser Arg Leu Thr Val Asp Lys Ser Arg Trp Gln Glu
                405                   410                   415
Gly Asn Val Phe Ser Cys Ser Val Met His Glu Ala Leu His Asn His
                420                   425                   430
Tyr Thr Gln Lys Ser Leu Ser Leu Ser Leu Gly Lys
                435                   440
```

<210> SEQ ID NO 5
<211> LENGTH: 642
<212> TYPE: DNA
<213> ORGANISM: Artificial Sequence
<220> FEATURE:
<223> OTHER INFORMATION: DNA sequence of a light chain of anti-CD47
      antibody

<400> SEQUENCE: 5

-continued

```
gagatcgtgc tgacccagtc tccagccaca ctgtctctgt ccccaggaga gagggccacc        60
ctgagctgcc gggcttctga gaacgtgggc acatacatct cctggtatca gcagaagcca       120
ggacaggctc ctaggctgct gatctacggc gctagcaata gatataccgg catccctgct       180
cgcttcagcg gatctggatc cggcacagac tttaccctga caatctccag cctggagcca       240
gaggatttcg ccgtgtacta ttgtggcgag tcctacggcc acctgtatac ctttggcggc       300
ggcacaaagg tggagatcaa gcgaacggtg gctgcaccat ctgtcttcat cttcccgcca       360
tctgatgagc agttgaaatc tggaactgcc tctgttgtgt gcctgctgaa taacttctat       420
cccagagagg ccaaagtaca gtggaaggtg gataacgccc tccaatcggg taactcccag       480
gagagtgtca cagagcagga cagcaaggac agcacctaca gcctcagcag caccctgacg       540
ctgagcaaag cagactacga gaaacacaaa gtctacgcct gcgaagtcac ccatcagggc       600
ctgagctcgc ccgtcacaaa gagcttcaac aggggagagt gt                          642
```

<210> SEQ ID NO 6
<211> LENGTH: 214
<212> TYPE: PRT
<213> ORGANISM: Artificial Sequence
<220> FEATURE:
<223> OTHER INFORMATION: Amino acid sequence of a light chain of
      anti-CD47 antibody (L0)

<400> SEQUENCE: 6

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Asn Val Gly Thr Tyr
            20                  25                  30

Ile Ser Trp Tyr Gln Gln Lys Pro Gly Gln Ala Pro Arg Leu Leu Ile
        35                  40                  45

Tyr Gly Ala Ser Asn Arg Tyr Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gly Glu Ser Tyr Gly His Leu Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 7
<211> LENGTH: 1752
<212> TYPE: DNA

-continued

<213> ORGANISM: Artificial Sequence
<220> FEATURE:
<223> OTHER INFORMATION: DNA sequence of polypeptide chain H1

<400> SEQUENCE: 7
gaggtgcagc tggtgcagtc cggagctgag gtgaagaagc caggatccag cgtgaaggtg      60
agctgcaagg ctagcggcta ctctttcacc caccattgga tccactgggt gaggcaggct     120
cctggacagg gactggagtg gatgggcatg atcgacgctt ccgatagcga gacaagactg     180
tctcagaagt ttaaggaccg cgtgaccatc acagccgata agtctacctc cacagcttac     240
atggagctgt cttccctgag atccgaggac accgccgtgt actattgtgc taggctgggc     300
cggtactatt tcgattattg gggccagggc accacagtga cagtgagctc tgccagcaca     360
aagggccctt ccgtgttccc actggctccc tgctccagaa gcacatctga gtccaccgcc     420
gctctgggct gtctggtgaa ggactacttc cctgagccag tgaccgtgtc ctggaacagc     480
ggcgccctga catctggcgt gcacaccttt ccagctgtgc tgcagtccag cggcctgtac     540
tccctgtctt ccgtggtgac agtgcccagc tcttccctgg gcaccaagac atatacctgc     600
aacgtggacc ataagccttc caataccaag gtggataaga gggtggagag caagtacgga     660
ccaccttgcc caccatgtcc agctcctgag tttgagggag accatccgt gttcctgttt      720 cctccaaagc ctaaggacac cctgatgatc agccggacac ctgaggtgac ctgcgtggtg     780
gtggacgtgt ctcaggagga tccagaggtg cagttcaact ggtacgtgga tggcgtggag     840
gtgcacaatg ctaagaccaa gccaagagag gagcagttta attccacata ccgcgtggtg     900
agcgtgctga ccgtgctgca tcaggattgg ctgaacggca aggagtataa gtgcaaggtg     960
tccaataagg gcctgcccag ctctatcgag aagacaatca gcaaggctaa gggacagcct    1020
agggagccac aggtgtacac cctgccccct tctcaggagg agatgacaaa gaaccaggtg    1080
tccctgacct gtctggtgaa gggcttctat ccaagcgaca tcgctgtgga gtgggagtct    1140
aatggccagc ccgagaacaa ttacaagacc acaccacccg tgctggactc tgatggctcc    1200
ttctttctgt attctaggct gacagtggat aagtcccggt ggcaggaggg caacgtgttt    1260
agctgctctg tgatgcacga ggccctgcac aatcattata cccagaagtc cctgagcctg    1320
tctctgggca aggaacctaa gtctagcgac aaaactcata ccagcccccc tagtccagag    1380
gtgcagctgg tggagtctgg aggaggactg gtgcagccag aggcagcct gaggctgtct     1440 tgcgccgctt ccggctacaa gtatggcgtg tactccatgg atggttcag gcaggctcct     1500 ggcaagggac tggagggcgt gtccgccatc tgttctggcg gcagaaccac atactctgac    1560
tccgtgaagg gcaggtttac catctcccgg ataacagca accagatcct gtatctgcag     1620
atgaactccc tgagagccga ggacaccgcc gtgtactatt gcgctgctag gccactgtgg    1680
acaggcgact gtgatctgtc cagctcttgg tataagacct ggggccaggg caccctggtg    1740
acagtgtcca gc                                                       1752

<210> SEQ ID NO 8
<211> LENGTH: 584
<212> TYPE: PRT
<213> ORGANISM: Artificial Sequence
<220> FEATURE:
<223> OTHER INFORMATION: Amino acid sequence of polypeptide chain H1

<400> SEQUENCE: 8

Glu Val Gln Leu Val Gln Ser Gly Ala Glu Val Lys Lys Pro Gly Ser
1               5                   10                  15

-continued

```
Ser Val Lys Val Ser Cys Lys Ala Ser Gly Tyr Ser Phe Thr His His
        20                  25                  30

Trp Ile His Trp Val Arg Gln Ala Pro Gly Gln Gly Leu Glu Trp Met
        35                  40                  45

Gly Met Ile Asp Ala Ser Asp Ser Glu Thr Arg Leu Ser Gln Lys Phe
        50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly Arg Tyr Tyr Phe Asp Tyr Trp Gly Gln Gly Thr Thr
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
        210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys Glu Pro Lys Ser
```

-continued

```
             435                440                445
Ser Asp Lys Thr His Thr Ser Pro Pro Ser Pro Glu Val Gln Leu Val
    450                455                460
Glu Ser Gly Gly Gly Leu Val Gln Pro Gly Gly Ser Leu Arg Leu Ser
465                470                475                480
Cys Ala Ala Ser Gly Tyr Lys Tyr Gly Val Tyr Ser Met Gly Trp Phe
                485                490                495
Arg Gln Ala Pro Gly Lys Gly Leu Glu Gly Val Ser Ala Ile Cys Ser
            500                505                510
Gly Gly Arg Thr Thr Tyr Ser Asp Ser Val Lys Gly Arg Phe Thr Ile
            515                520                525
Ser Arg Asp Asn Ser Asn Gln Ile Leu Tyr Leu Gln Met Asn Ser Leu
        530                535                540
Arg Ala Glu Asp Thr Ala Val Tyr Tyr Cys Ala Ala Arg Pro Leu Trp
545                550                555                560
Thr Gly Asp Cys Asp Leu Ser Ser Ser Trp Tyr Lys Thr Trp Gly Gln
            565                570                575
Gly Thr Leu Val Thr Val Ser Ser
            580
```

<210> SEQ ID NO 9
<211> LENGTH: 1752
<212> TYPE: DNA
<213> ORGANISM: Artificial Sequence
<220> FEATURE:
<223> OTHER INFORMATION: DNA sequence of polypeptide chain H2

<400> SEQUENCE: 9

```
gaggtgcagc tggtggagtc tggaggagga ctggtgcagc caggaggcag cctgaggctg      60
tcttgcgccg cttccggcta caagtatggc gtgtactcca tgggatggtt caggcaggct     120
cctggcaagg gactggaggg cgtgtccgcc atctgttctg gcggcagaac cacatactct     180
gactccgtga agggcaggtt taccatctcc cgggataaca gcaaccagat cctgtatctg     240
cagatgaact ccctgagagc cgaggacacc gccgtgtact attgcgctgc taggccactg     300
tggacaggcg actgtgatct gtccagctct tggtataaga cctggggcca gggcaccctg     360
gtgacagtgt ccagcgaacc taagtctagc gacaaaactc ataccagccc ccctagtcca     420
gaggtgcagc tggtgcagtc cggagctgag gtgaagaagc aggatccag cgtgaaggtg      480 agctgcaagg ctagcggcta ctctttcacc caccattgga tccactgggt gaggcaggct     540
cctggacagg gactggagtg gatgggcatg atcgacgctt ccgatagcga gacaagactg     600
tctcagaagt ttaaggaccg cgtgaccatc acagccgata gtctacctc cacagcttac      660 atggagctgt cttccctgag atccgaggac accgccgtgt actattgtgc taggctgggc     720
cggtactatt tcgattattg gggccagggc accacagtga cagtgagctc tgccagcaca     780
aagggccctt ccgtgttccc actggctccc tgctccagaa gcacatctga gtccaccgcc     840
gctctgggct gtctggtgaa ggactacttc cctgagccag tgaccgtgtc ctggaacagc     900
ggcgccctga catctggcgt gcacaccttt ccagctgtgc tgcagtccag cggcctgtac     960
tccctgtctt ccgtggtgac agtgcccagc tcttccctgg gcaccaagac atatacctgc    1020
aacgtggacc ataagccttc caataccaag gtggataaga gggtggagag caagtacgga    1080 ccacccttgcc caccatgtcc agctcctgag tttgagggag accatccgt gttcctgttt    1140 cctccaaagc ctaaggacac cctgatgatc agccggacac ctgaggtgac ctgcgtggtg    1200
```

```
gtggacgtgt ctcaggagga tccagaggtg cagttcaact ggtacgtgga tggcgtggag   1260
gtgcacaatg ctaagaccaa gccaagagag gagcagttta attccacata ccgcgtggtg   1320
agcgtgctga ccgtgctgca tcaggattgg ctgaacggca aggagtataa gtgcaaggtg   1380
tccaataagg gcctgcccag ctctatcgag aagacaatca gcaaggctaa gggacagcct   1440
agggagccac aggtgtacac cctgccccct tctcaggagg agatgacaaa gaaccaggtg   1500
tccctgacct gtctggtgaa gggcttctat ccaagcgaca tcgctgtgga gtgggagtct   1560
aatggccagc ccgagaacaa ttacaagacc acaccacccg tgctggactc tgatggctcc   1620
ttctttctgt attctaggct gacagtggat aagtcccggt ggcaggaggg caacgtgttt   1680
agctgctctg tgatgcacga ggccctgcac aatcattata cccagaagtc cctgagcctg   1740
tctctgggca ag                                                       1752
```

```
<210> SEQ ID NO 10
<211> LENGTH: 584
<212> TYPE: PRT
<213> ORGANISM: Artificial Sequence
<220> FEATURE:
<223> OTHER INFORMATION: Amino acid sequence of polypeptide chain H2

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ser Asn Gln Ile Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
            100                 105                 110

Lys Thr Trp Gly Gln Gly Thr Leu Val Thr Val Ser Ser Glu Pro Lys
        115                 120                 125

Ser Ser Asp Lys Thr His Thr Ser Pro Pro Ser Pro Glu Val Gln Leu
    130                 135                 140

Val Gln Ser Gly Ala Glu Val Lys Lys Pro Gly Ser Ser Val Lys Val
145                 150                 155                 160

Ser Cys Lys Ala Ser Gly Tyr Ser Phe Thr His His Trp Ile His Trp
                165                 170                 175

Val Arg Gln Ala Pro Gly Gln Gly Leu Glu Trp Met Gly Met Ile Asp
            180                 185                 190

Ala Ser Asp Ser Glu Thr Arg Leu Ser Gln Lys Phe Lys Asp Arg Val
            195                 200                 205

Thr Ile Thr Ala Asp Lys Ser Thr Ser Thr Ala Tyr Met Glu Leu Ser
    210                 215                 220

Ser Leu Arg Ser Glu Asp Thr Ala Val Tyr Tyr Cys Ala Arg Leu Gly
225                 230                 235                 240

Arg Tyr Tyr Phe Asp Tyr Trp Gly Gln Gly Thr Thr Val Thr Val Ser
            245                 250                 255

Ser Ala Ser Thr Lys Gly Pro Ser Val Phe Pro Leu Ala Pro Cys Ser
```

```
              260            265           270
Arg Ser Thr Ser Glu Ser Thr Ala Ala Leu Gly Cys Leu Val Lys Asp
        275           280           285
Tyr Phe Pro Glu Pro Val Thr Val Ser Trp Asn Ser Gly Ala Leu Thr
    290           295           300
Ser Gly Val His Thr Phe Pro Ala Val Leu Gln Ser Ser Gly Leu Tyr
305           310           315           320
Ser Leu Ser Ser Val Val Thr Val Pro Ser Ser Ser Leu Gly Thr Lys
            325           330           335
Thr Tyr Thr Cys Asn Val Asp His Lys Pro Ser Asn Thr Lys Val Asp
            340           345           350
Lys Arg Val Glu Ser Lys Tyr Gly Pro Pro Cys Pro Pro Cys Pro Ala
            355           360           365
Pro Glu Phe Glu Gly Gly Pro Ser Val Phe Leu Phe Pro Pro Lys Pro
        370           375           380
Lys Asp Thr Leu Met Ile Ser Arg Thr Pro Glu Val Thr Cys Val Val
385           390           395           400
Val Asp Val Ser Gln Glu Asp Pro Glu Val Gln Phe Asn Trp Tyr Val
            405           410           415
Asp Gly Val Glu Val His Asn Ala Lys Thr Lys Pro Arg Glu Glu Gln
            420           425           430
Phe Asn Ser Thr Tyr Arg Val Val Ser Val Leu Thr Val Leu His Gln
        435           440           445
Asp Trp Leu Asn Gly Lys Glu Tyr Lys Cys Lys Val Ser Asn Lys Gly
    450           455           460
Leu Pro Ser Ser Ile Glu Lys Thr Ile Ser Lys Ala Lys Gly Gln Pro
465           470           475           480
Arg Glu Pro Gln Val Tyr Thr Leu Pro Pro Ser Gln Glu Glu Met Thr
            485           490           495
Lys Asn Gln Val Ser Leu Thr Cys Leu Val Lys Gly Phe Tyr Pro Ser
            500           505           510
Asp Ile Ala Val Glu Trp Glu Ser Asn Gly Gln Pro Glu Asn Asn Tyr
        515           520           525
Lys Thr Thr Pro Pro Val Leu Asp Ser Asp Gly Ser Phe Phe Leu Tyr
        530           535           540
Ser Arg Leu Thr Val Asp Lys Ser Arg Trp Gln Glu Gly Asn Val Phe
545           550           555           560
Ser Cys Ser Val Met His Glu Ala Leu His Asn His Tyr Thr Gln Lys
            565           570           575
Ser Leu Ser Leu Ser Leu Gly Lys
            580
```

<210> SEQ ID NO 11
<211> LENGTH: 1734
<212> TYPE: DNA
<213> ORGANISM: Artificial Sequence
<220> FEATURE:
<223> OTHER INFORMATION: DNA sequence of polypeptide chain H3

<400> SEQUENCE: 11

```
gaggtgcagc tggtgcagtc cggagctgag gtgaagaagc caggatccag cgtgaaggtg      60
agctgcaagg ctagcggcta ctctttcacc caccattgga tccactgggt gaggcaggct     120
cctggacagg gactggagtg gatgggcatg atcgacgctt ccgatagcga gacaagactg     180
tctcagaagt ttaaggaccg cgtgaccatc acagccgata agtctacctc cacagcttac     240
```

-continued

```
atggagctgt cttccctgag atccgaggac accgccgtgt actattgtgc taggctgggc     300
cggtactatt tcgattattg gggccagggc accacagtga cagtgagctc tgccagcaca     360
aagggccctt ccgtgttccc actggctccc tgctccagaa gcacatctga gtccaccgcc     420
gctctgggct gtctggtgaa ggactacttc cctgagccag tgaccgtgtc ctggaacagc     480
ggcgccctga catctggcgt gcacaccttt ccagctgtgc tgcagtccag cggcctgtac     540
tccctgtctt ccgtggtgac agtgcccagc tcttccctgg gcaccaagac atatacctgc     600
aacgtggacc ataagccttc caataccaag gtggataaga gggtggagag caagtacgga     660
ccaccttgcc caccatgtcc agctcctgag tttgagggag accatccgt gttcctgttt      720 cctccaaagc ctaaggacac cctgatgatc agccggacac ctgaggtgac ctgcgtggtg     780
gtggacgtgt ctcaggagga tccagaggtg cagttcaact ggtacgtgga tggcgtggag     840
gtgcacaatg ctaagaccaa gccaagagag gagcagttta attccacata ccgcgtggtg     900
agcgtgctga ccgtgctgca tcaggattgg ctgaacggca aggagtataa gtgcaaggtg     960
tccaataagg gcctgcccag ctctatcgag aagacaatca gcaaggctaa gggacagcct    1020
agggagccac aggtgtacac cctgcccccct tctcaggagg agatgacaaa gaaccaggtg   1080
tccctgacct gtctggtgaa gggcttctat ccaagcgaca tcgctgtgga gtgggagtct    1140
aatggccagc ccgagaacaa ttacaagacc acaccacccg tgctggactc tgatggctcc    1200
ttctttctgt attctaggct gacagtggat aagtcccggt ggcaggaggg caacgtgttt    1260
agctgctctg tgatgcacga ggccctgcac aatcattata cccagaagtc cctgagcctg    1320
tctctgggca agggtggagg cggtagtgga ggcggttcag aggtgcagct ggtggagtct    1380
ggaggaggac tggtgcagcc aggaggcagc ctgaggctgt cttgcgccgc ttccggctac    1440
aagtatggcg tgtactccat gggatggttc aggcaggctc ctggcaaggg actggagggc    1500
gtgtccgcca tctgttctgg cggcagaacc acatactctg actccgtgaa gggcaggttt    1560
accatctccc gggataacag caaccagatc ctgtatctgc agatgaactc cctgagagcc    1620
gaggacaccg ccgtgtacta ttgcgctgct aggccactgt ggacaggcga ctgtgatctg    1680
tccagctctt ggtataagac ctggggccag ggcacccctgg tgacagtgtc cagc          1734
```

<210> SEQ ID NO 12
<211> LENGTH: 578
<212> TYPE: PRT
<213> ORGANISM: Artificial Sequence
<220> FEATURE:
<223> OTHER INFORMATION: Amino acid sequence of polypeptide chain H3

<400> SEQUENCE: 12

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr His His
            20                  25                  30

Trp Ile His Trp Val Arg Gln Ala Pro Gly Gln Gly Leu Glu Trp Met
        35                  40                  45

Gly Met Ile Asp Ala Ser Asp Ser Glu Thr Arg Leu Ser Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

-continued

```
Ala Arg Leu Gly Arg Tyr Tyr Phe Asp Tyr Trp Gly Gln Gly Thr Thr
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
        210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys Gly Gly Gly Gly
        435                 440                 445

Ser Gly Gly Gly Ser Glu Val Gln Leu Val Glu Ser Gly Gly Gly Leu
    450                 455                 460

Val Gln Pro Gly Gly Ser Leu Arg Leu Ser Cys Ala Ala Ser Gly Tyr
465                 470                 475                 480

Lys Tyr Gly Val Tyr Ser Met Gly Trp Phe Arg Gln Ala Pro Gly Lys
                485                 490                 495

Gly Leu Glu Gly Val Ser Ala Ile Cys Ser Gly Gly Arg Thr Thr Tyr
            500                 505                 510

Ser Asp Ser Val Lys Gly Arg Phe Thr Ile Ser Arg Asp Asn Ser Asn
```

```
              515              520              525
Gln Ile Leu Tyr Leu Gln Met Asn Ser Leu Arg Ala Glu Asp Thr Ala
    530              535              540

Val Tyr Tyr Cys Ala Ala Arg Pro Leu Trp Thr Gly Asp Cys Asp Leu
545              550              555              560

Ser Ser Ser Trp Tyr Lys Thr Trp Gly Gln Gly Thr Leu Val Thr Val
              565              570              575

Ser Ser
```

<210> SEQ ID NO 13
<211> LENGTH: 1734
<212> TYPE: DNA
<213> ORGANISM: Artificial Sequence
<220> FEATURE:
<223> OTHER INFORMATION: DNA sequence of polypeptide chain H4

<400> SEQUENCE: 13

```
gaggtgcagc tggtggagtc tggaggagga ctggtgcagc caggaggcag cctgaggctg      60
tcttgcgccg cttccggcta caagtatggc gtgtactcca tgggatggtt caggcaggct     120
cctggcaagg gactggaggg cgtgtccgcc atctgttctg cggcagaac cacatactct      180 gactccgtga agggcaggtt taccatctcc cgggataaca gcaaccagat cctgtatctg      240
cagatgaact ccctgagagc cgaggacacc gccgtgtact attgcgctgc taggccactg      300
tggacaggcg actgtgatct gtccagctct tggtataaga cctggggcca gggcaccctg      360
gtgacagtgt ccagcggtgg aggcggtagt ggaggcggtt cagaggtgca gctggtgcag      420
tccggagctg aggtgaagaa gccaggatcc agcgtgaagg tgagctgcaa ggctagcggc      480
tactctttca cccaccattg gatccactgg gtgaggcagg ctcctggaca gggactggag      540
tggatgggca tgatcgacgc ttccgatagc gagacaagac tgtctcagaa gtttaaggac      600
cgcgtgacca tcacagccga taagtctacc tccacagctt acatggagct gtcttccctg      660
agatccgagg acaccgccgt gtactattgt gctaggctgg ccggtacta tttcgattat      720 tggggccagg gcaccacagt gacagtgagc tctgccagca caaagggccc ttccgtgttc      780
ccactggctc cctgctccag aagcacatct gagtccaccg ccgctctggg ctgtctggtg      840
aaggactact ccctgagcc agtgaccgtg tcctggaaca gcggcgccct gacatctggc      900
gtgcacacct tccagctgt gctgcagtcc agcggcctgt actccctgtc ttccgtggtg      960
acagtgccca gctcttccct gggcaccaag acatatacct gcaacgtgga ccataagcct     1020
tccaatacca aggtggataa gagggtggag agcaagtacg gaccaccttg cccaccatgt     1080
ccagctcctg agtttgaggg aggaccatcc gtgttcctgt ttcctccaaa gcctaaggac     1140
accctgatga tcagccggac acctgaggtg acctgcgtgg tggtggacgt gtctcaggag     1200
gatccagagg tgcagttcaa ctggtacgtg gatggcgtgg aggtgcacaa tgctaagacc     1260
aagccaagag aggagcagtt taattccaca taccgcgtgg tgagcgtgct gaccgtgctg     1320
catcaggatt ggctgaacgg caaggagtat aagtgcaagg tgtccaataa gggcctgccc     1380
agctctatcg agaagacaat cagcaaggct aagggacagc ctaggagcc acaggtgtac     1440 accctgcccc cttctcagga ggagatgaca aagaaccagg tgtccctgac ctgtctggtg     1500
aagggcttct atccaagcga catcgctgtg gagtgggagt ctaatggcca gcccgagaac     1560
aattacaaga ccacaccacc cgtgctggac tctgatggct ccttcttct gtattctagg     1620 ctgacagtgg ataagtcccg gtggcaggag ggcaacgtgt ttagctgctc tgtgatgcac     1680
```

-continued gaggccctgc acaatcatta tacccagaag tccctgagcc tgtctctggg caag          1734

<210> SEQ ID NO 14
<211> LENGTH: 578
<212> TYPE: PRT
<213> ORGANISM: Artificial Sequence
<220> FEATURE:
<223> OTHER INFORMATION: Amino acid sequence of polypeptide chain H4

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ser Asn Gln Ile Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
            100                 105                 110

Lys Thr Trp Gly Gln Gly Thr Leu Val Thr Val Ser Ser Gly Gly Gly
            115                 120                 125

Gly Ser Gly Gly Gly Ser Glu Val Gln Leu Val Gln Ser Gly Ala Glu
        130                 135                 140

Val Lys Lys Pro Gly Ser Ser Val Lys Val Ser Cys Lys Ala Ser Gly
145                 150                 155                 160

Tyr Ser Phe Thr His His Trp Ile His Trp Val Arg Gln Ala Pro Gly
                165                 170                 175

Gln Gly Leu Glu Trp Met Gly Met Ile Asp Ala Ser Asp Ser Glu Thr
            180                 185                 190

Arg Leu Ser Gln Lys Phe Lys Asp Arg Val Thr Ile Thr Ala Asp Lys
            195                 200                 205

Ser Thr Ser Thr Ala Tyr Met Glu Leu Ser Ser Leu Arg Ser Glu Asp
    210                 215                 220

Thr Ala Val Tyr Tyr Cys Ala Arg Leu Gly Arg Tyr Tyr Phe Asp Tyr
225                 230                 235                 240

Trp Gly Gln Gly Thr Thr Val Thr Val Ser Ser Ala Ser Thr Lys Gly
            245                 250                 255

Pro Ser Val Phe Pro Leu Ala Pro Cys Ser Arg Ser Thr Ser Glu Ser
            260                 265                 270

Thr Ala Ala Leu Gly Cys Leu Val Lys Asp Tyr Phe Pro Glu Pro Val
        275                 280                 285

Thr Val Ser Trp Asn Ser Gly Ala Leu Thr Ser Gly Val His Thr Phe
    290                 295                 300

Pro Ala Val Leu Gln Ser Ser Gly Leu Tyr Ser Leu Ser Ser Val Val
305                 310                 315                 320

Thr Val Pro Ser Ser Ser Leu Gly Thr Lys Thr Tyr Thr Cys Asn Val
                325                 330                 335

Asp His Lys Pro Ser Asn Thr Lys Val Asp Lys Arg Val Glu Ser Lys
            340                 345                 350

Tyr Gly Pro Pro Cys Pro Pro Cys Pro Ala Pro Glu Phe Glu Gly Gly

```
              355                 360                 365
Pro Ser Val Phe Leu Phe Pro Pro Lys Pro Lys Asp Thr Leu Met Ile
    370                 375                 380

Ser Arg Thr Pro Glu Val Thr Cys Val Val Val Asp Val Ser Gln Glu
385                 390                 395                 400

Asp Pro Glu Val Gln Phe Asn Trp Tyr Val Asp Gly Val Glu Val His
                405                 410                 415

Asn Ala Lys Thr Lys Pro Arg Glu Glu Gln Phe Asn Ser Thr Tyr Arg
            420                 425                 430

Val Val Ser Val Leu Thr Val Leu His Gln Asp Trp Leu Asn Gly Lys
            435                 440                 445

Glu Tyr Lys Cys Lys Val Ser Asn Lys Gly Leu Pro Ser Ser Ile Glu
    450                 455                 460

Lys Thr Ile Ser Lys Ala Lys Gly Gln Pro Arg Glu Pro Gln Val Tyr
465                 470                 475                 480

Thr Leu Pro Pro Ser Gln Glu Glu Met Thr Lys Asn Gln Val Ser Leu
                485                 490                 495

Thr Cys Leu Val Lys Gly Phe Tyr Pro Ser Asp Ile Ala Val Glu Trp
            500                 505                 510

Glu Ser Asn Gly Gln Pro Glu Asn Asn Tyr Lys Thr Thr Pro Pro Val
            515                 520                 525

Leu Asp Ser Asp Gly Ser Phe Phe Leu Tyr Ser Arg Leu Thr Val Asp
    530                 535                 540

Lys Ser Arg Trp Gln Glu Gly Asn Val Phe Ser Cys Ser Val Met His
545                 550                 555                 560

Glu Ala Leu His Asn His Tyr Thr Gln Lys Ser Leu Ser Leu Ser Leu
                565                 570                 575

Gly Lys
```

```
<210> SEQ ID NO 15
<211> LENGTH: 1062
<212> TYPE: DNA
<213> ORGANISM: Artificial Sequence
<220> FEATURE:
<223> OTHER INFORMATION: DNA sequence of polypeptide chain L1

<400> SEQUENCE: 15
gagatcgtgc tgacccagtc tccagccaca ctgtctctgt ccccaggaga gagggccacc      60
ctgagctgcc gggcttctga aacgtgggc acatacatct cctggtatca gcagaagcca     120
ggacaggctc ctaggctgct gatctacggc gctagcaata gatataccgg catccctgct     180
cgcttcagcg gatctggatc cggcacagac tttaccctga caatctccag cctggagcca     240
gaggatttcg ccgtgtacta ttgtggcgag tcctacggcc acctgtatac ctttggcggc     300
ggcacaaagg tggagatcaa gcgaacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gtgaacctaa gtctagcgac     660
aaaactcata ccagcccccc cagtccagag gtgcagctgg tggagtctgg aggaggactg     720
gtgcagccag gaggcagcct gaggctgtct tgcgccgctt ccggctacaa gtatggcgtg     780
```

```
tactccatgg gatggttcag gcaggctcct ggcaagggac tggagggcgt gtccgccatc      840
tgttctggcg gcagaaccac atactctgac tccgtgaagg gcaggtttac catctcccgg      900
gataacagca accagatcct gtatctgcag atgaactccc tgagagccga ggacaccgcc      960
gtgtactatt gcgctgctag gccactgtgg acaggcgact gtgatctgtc cagctcttgg     1020
tataagacct ggggccaggg caccctggtg acagtgtcca gc                        1062
```

```
<210> SEQ ID NO 16
<211> LENGTH: 354
<212> TYPE: PRT
<213> ORGANISM: Artificial Sequence
<220> FEATURE:
<223> OTHER INFORMATION: Amino acid sequence of polypeptide chain L1

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Asn Val Gly Thr Tyr
            20                  25                  30

Ile Ser Trp Tyr Gln Gln Lys Pro Gly Gln Ala Pro Arg Leu Leu Ile
        35                  40                  45

Tyr Gly Ala Ser Asn Arg Tyr Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gly Glu Ser Tyr Gly His Leu Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Glu Pro Lys Ser Ser Asp Lys Thr His Thr
        210                 215                 220

Ser Pro Pro Ser Pro Glu Val Gln Leu Val Glu Ser Gly Gly Gly Leu
225                 230                 235                 240

Val Gln Pro Gly Gly Ser Leu Arg Leu Ser Cys Ala Ala Ser Gly Tyr
                245                 250                 255

Lys Tyr Gly Val Tyr Ser Met Gly Trp Phe Arg Gln Ala Pro Gly Lys
            260                 265                 270

Gly Leu Glu Gly Val Ser Ala Ile Cys Ser Gly Gly Arg Thr Thr Tyr
            275                 280                 285

Ser Asp Ser Val Lys Gly Arg Phe Thr Ile Ser Arg Asp Asn Ser Asn
        290                 295                 300

Gln Ile Leu Tyr Leu Gln Met Asn Ser Leu Arg Ala Glu Asp Thr Ala
305                 310                 315                 320
```

```
Val Tyr Tyr Cys Ala Ala Arg Pro Leu Trp Thr Gly Asp Cys Asp Leu
                325                 330                 335

Ser Ser Ser Trp Tyr Lys Thr Trp Gly Gln Gly Thr Leu Val Thr Val
                340                 345                 350

Ser Ser
```

```
<210> SEQ ID NO 17
<211> LENGTH: 1062
<212> TYPE: DNA
<213> ORGANISM: Artificial Sequence
<220> FEATURE:
<223> OTHER INFORMATION: DNA sequence of polypeptide chain L2

<400> SEQUENCE: 17
gaggtgcagc tggtggagtc tggaggagga ctggtgcagc caggaggcag cctgaggctg      60
tcttgcgccg cttccggcta caagtatggc gtgtactcca tgggatggtt caggcaggct     120
cctggcaagg gactggaggg cgtgtccgcc atctgttctg cggcagaac cacatactct      180 gactccgtga agggcaggtt taccatctcc cgggataaca gcaaccagat cctgtatctg     240
cagatgaact ccctgagagc cgaggacacc gccgtgtact attgcgctgc taggccactg     300
tggacaggcg actgtgatct gtccagctct tggtataaga cctggggcca gggcaccctg     360
gtgacagtgt ccagcgaacc taagtctagc gacaaaactc ataccagccc ccctagtcca     420
gagatcgtgc tgacccagtc tccagccaca ctgtctctgt ccccaggaga gagggccacc     480
ctgagctgcc gggcttctga aacgtgggc acatacatct cctggtatca gcagaagcca     540
ggacaggctc ctaggctgct gatctacggc gctagcaata gatataccgg catccctgct     600
cgcttcagcg gatctggatc cggcacagac tttaccctga caatctccag cctggagcca     660
gaggatttcg ccgtgtacta ttgtggcgag tcctacggcc acctgtatac ctttggcggc     720
ggcacaaagg tggagatcaa gcgaacggtg gctgcaccat ctgtcttcat cttcccgcca     780
tctgatgagc agttgaaatc tggaactgcc tctgttgtgt gcctgctgaa taacttctat     840
cccagagagg ccaaagtaca gtggaaggtg gataacgccc tccaatcggg taactcccag     900
gagagtgtca cagagcagga cagcaaggac agcacctaca gcctcagcag caccctgacg     960
ctgagcaaag cagactacga gaaacacaaa gtctacgcct gcgaagtcac ccatcagggc    1020
ctgagctcgc ccgtcacaaa gagcttcaac aggggagagt gt                       1062
```

```
<210> SEQ ID NO 18
<211> LENGTH: 354
<212> TYPE: PRT
<213> ORGANISM: Artificial Sequence
<220> FEATURE:
<223> OTHER INFORMATION: Amino acid sequence of polypeptide chain L2

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
                20                  25                  30

Ser Met Gly Trp Phe Arg Gln Ala Pro Gly Lys Gly Leu Glu Gly Val
                35                  40                  45

Ser Ala Ile Cys Ser Gly Gly Arg Thr Thr Tyr Ser Asp Ser Val Lys
            50                  55                  60

Gly Arg Phe Thr Ile Ser Arg Asp Asn Ser Asn Gln Ile Leu Tyr Leu
65                  70                  75                  80
```

-continued

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
            100                 105                 110

Lys Thr Trp Gly Gln Gly Thr Leu Val Thr Val Ser Ser Glu Pro Lys
        115                 120                 125

Ser Ser Asp Lys Thr His Thr Ser Pro Pro Ser Pro Glu Ile Val Leu
    130                 135                 140

Thr Gln Ser Pro Ala Thr Leu Ser Leu Ser Pro Gly Glu Arg Ala Thr
145                 150                 155                 160

Leu Ser Cys Arg Ala Ser Glu Asn Val Gly Thr Tyr Ile Ser Trp Tyr
            165                 170                 175

Gln Gln Lys Pro Gly Gln Ala Pro Arg Leu Leu Ile Tyr Gly Ala Ser
            180                 185                 190

Asn Arg Tyr Thr Gly Ile Pro Ala Arg Phe Ser Gly Ser Gly Ser Gly
            195                 200                 205

Thr Asp Phe Thr Leu Thr Ile Ser Ser Leu Glu Pro Glu Asp Phe Ala
    210                 215                 220

Val Tyr Tyr Cys Gly Glu Ser Tyr Gly His Leu Tyr Thr Phe Gly Gly
225                 230                 235                 240

Gly Thr Lys Val Glu Ile Lys Arg Thr Val Ala Ala Pro Ser Val Phe
            245                 250                 255

Ile Phe Pro Pro Ser Asp Glu Gln Leu Lys Ser Gly Thr Ala Ser Val
            260                 265                 270

Val Cys Leu Leu Asn Asn Phe Tyr Pro Arg Glu Ala Lys Val Gln Trp
            275                 280                 285

Lys Val Asp Asn Ala Leu Gln Ser Gly Asn Ser Gln Glu Ser Val Thr
    290                 295                 300

Glu Gln Asp Ser Lys Asp Ser Thr Tyr Ser Leu Ser Ser Thr Leu Thr
305                 310                 315                 320

Leu Ser Lys Ala Asp Tyr Glu Lys His Lys Val Tyr Ala Cys Glu Val
            325                 330                 335

Thr His Gln Gly Leu Ser Ser Pro Val Thr Lys Ser Phe Asn Arg Gly
            340                 345                 350

Glu Cys

<210> SEQ ID NO 19
<211> LENGTH: 1044
<212> TYPE: DNA
<213> ORGANISM: Artificial Sequence
<220> FEATURE:
<223> OTHER INFORMATION: DNA sequence of polypeptide chain L3

<400> SEQUENCE: 19
gagatcgtgc tgacccagtc tccagccaca ctgtctctgt ccccaggaga gagggccacc      60
ctgagctgcc gggcttctga gaacgtgggc acatacatct cctggtatca gcagaagcca     120
ggacaggctc ctaggctgct gatctacggc gctagcaata gatataccgg catccctgct     180
cgcttcagcg gatctggatc cggcacagac tttaccctga caatctccag cctggagcca     240
gaggatttcg ccgtgtacta ttgtggcgag tcctacggcc acctgtatac ctttggcggc     300
ggcacaaagg tggagatcaa gcgaacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc ccaatcgggt aactcccag     480

```
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gtggtggagg cggtagtgga    660
ggcggttcag aggtgcagct ggtggagtct ggaggaggac tggtgcagcc aggaggcagc    720
ctgaggctgt cttgcgccgc ttccggctac aagtatggcg tgtactccat gggatggttc    780
aggcaggctc ctggcaaggg actggagggc gtgtccgcca tctgttctgg cggcagaacc    840
acatactctg actccgtgaa gggcaggttt accatctccc gggataacag caaccagatc    900
ctgtatctgc agatgaactc cctgagagcc gaggacaccg ccgtgtacta ttgcgctgct    960
aggccactgt ggacaggcga ctgtgatctg tccagctctt ggtataagac ctggggccag   1020
ggcaccctgg tgacagtgtc cagc                                         1044
```

<210> SEQ ID NO 20
<211> LENGTH: 348
<212> TYPE: PRT
<213> ORGANISM: Artificial Sequence
<220> FEATURE:
<223> OTHER INFORMATION: Amino acid sequence of polypeptide chain L3

<400> SEQUENCE: 20

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Asn Val Gly Thr Tyr
            20                  25                  30

Ile Ser Trp Tyr Gln Gln Lys Pro Gly Gln Ala Pro Arg Leu Leu Ile
        35                  40                  45

Tyr Gly Ala Ser Asn Arg Tyr Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gly Glu Ser Tyr Gly His Leu Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Gly Gly Gly Gly Ser Gly Gly Gly Ser Glu
        210                 215                 220

Val Gln Leu Val Glu Ser Gly Gly Gly Leu Val Gln Pro Gly Gly Ser
225                 230                 235                 240

Leu Arg Leu Ser Cys Ala Ala Ser Gly Tyr Lys Tyr Gly Val Tyr Ser
            245                 250                 255
```

```
Met Gly Trp Phe Arg Gln Ala Pro Gly Lys Gly Leu Glu Gly Val Ser
          260                 265                 270

Ala Ile Cys Ser Gly Gly Arg Thr Thr Tyr Ser Asp Ser Val Lys Gly
          275                 280                 285

Arg Phe Thr Ile Ser Arg Asp Asn Ser Asn Gln Ile Leu Tyr Leu Gln
          290                 295                 300

Met Asn Ser Leu Arg Ala Glu Asp Thr Ala Val Tyr Tyr Cys Ala Ala
305                 310                 315                 320

Arg Pro Leu Trp Thr Gly Asp Cys Asp Leu Ser Ser Ser Trp Tyr Lys
                325                 330                 335

Thr Trp Gly Gln Gly Thr Leu Val Thr Val Ser Ser
          340                 345
```

```
<210> SEQ ID NO 21
<211> LENGTH: 1044
<212> TYPE: DNA
<213> ORGANISM: Artificial Sequence
<220> FEATURE:
<223> OTHER INFORMATION: DNA sequence of polypeptide chain L4

<400> SEQUENCE: 21
gaggtgcagc tggtggagtc tggaggagga ctggtgcagc caggaggcag cctgaggctg      60
tcttgcgccg cttccggcta caagtatggc gtgtactcca tgggatggtt caggcaggct     120
cctggcaagg gactggaggg cgtgtccgcc atctgttctg gcggcagaac cacatactct     180
gactccgtga agggcaggtt taccatctcc cgggataaca gcaaccagat cctgtatctg     240
cagatgaact ccctgagagc cgaggacacc gccgtgtact attgcgctgc taggccactg     300
tggacaggcg actgtgatct gtccagctct tggtataaga cctggggcca gggcaccctg     360
gtgacagtgt ccagcggtgg aggcggtagt ggaggcggtt cagagatcgt gctgacccag     420
tctccagcca cactgtctct gtccccagga gagagggcca ccctgagctg ccgggcttct     480
gagaacgtgg gcacatacat ctcctggtat cagcagaagc caggacaggc tcctaggctg     540
ctgatctacg gcgctagcaa tagatatacc ggcatccctg ctcgcttcag cggatctgga     600
tccggcacag actttaccct gacaatctcc agcctggagc agaggatttt cgccgtgtac     660
tattgtggcg agtcctacgg ccacctgtat acctttggcg gcggcacaaa ggtggagatc     720
aagcgaacgt ggctgcacc atctgtcttc atcttcccgc catctgatga gcagttgaaa     780
tctggaactg cctctgttgt gtgcctgctg aataacttct atcccagaga ggccaaagta     840
cagtggaagg tggataacgc cctccaatcg ggtaactccc aggagagtgt cacagagcag     900
gacagcaagg acagcaccta cagcctcagc agcaccctga cgctgagcaa agcagactac     960
gagaaacaca agtctacgc ctgcgaagtc acccatcagg gcctgagctc gcccgtcaca    1020
aagagcttca caggggagag tgt                                           1044
```

```
<210> SEQ ID NO 22
<211> LENGTH: 348
<212> TYPE: PRT
<213> ORGANISM: Artificial Sequence
<220> FEATURE:
<223> OTHER INFORMATION: Amino acid sequence of polypeptide chain L4

<400> SEQUENCE: 22

Glu Val Gln Leu Val Glu Ser Gly Gly Gly Leu Val Gln Pro Gly Gly
1                 5                 10                 15

Ser Leu Arg Leu Ser Cys Ala Ala Ser Gly Tyr Lys Tyr Gly Val Tyr
          20                 25                 30
```

```
Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys
        50                  55                  60

Gly Arg Phe Thr Ile Ser Arg Asp Asn Ser Asn Gln Ile Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
            100                 105                 110

Lys Thr Trp Gly Gln Gly Thr Leu Val Thr Val Ser Ser Gly Gly Gly
            115                 120                 125

Gly Ser Gly Gly Gly Ser Glu Ile Val Leu Thr Gln Ser Pro Ala Thr
            130                 135                 140

Leu Ser Leu Ser Pro Gly Glu Arg Ala Thr Leu Ser Cys Arg Ala Ser
145                 150                 155                 160

Glu Asn Val Gly Thr Tyr Ile Ser Trp Tyr Gln Gln Lys Pro Gly Gln
                165                 170                 175

Ala Pro Arg Leu Leu Ile Tyr Gly Ala Ser Asn Arg Tyr Thr Gly Ile
            180                 185                 190

Pro Ala Arg Phe Ser Gly Ser Gly Ser Gly Thr Asp Phe Thr Leu Thr
            195                 200                 205

Ile Ser Ser Leu Glu Pro Glu Asp Phe Ala Val Tyr Tyr Cys Gly Glu
    210                 215                 220

Ser Tyr Gly His Leu Tyr Thr Phe Gly Gly Gly Thr Lys Val Glu Ile
225                 230                 235                 240

Lys Arg Thr Val Ala Ala Pro Ser Val Phe Ile Phe Pro Pro Ser Asp
                245                 250                 255

Glu Gln Leu Lys Ser Gly Thr Ala Ser Val Val Cys Leu Leu Asn Asn
            260                 265                 270

Phe Tyr Pro Arg Glu Ala Lys Val Gln Trp Lys Val Asp Asn Ala Leu
            275                 280                 285

Gln Ser Gly Asn Ser Gln Glu Ser Val Thr Glu Gln Asp Ser Lys Asp
    290                 295                 300

Ser Thr Tyr Ser Leu Ser Ser Thr Leu Thr Leu Ser Lys Ala Asp Tyr
305                 310                 315                 320

Glu Lys His Lys Val Tyr Ala Cys Glu Val Thr His Gln Gly Leu Ser
                325                 330                 335

Ser Pro Val Thr Lys Ser Phe Asn Arg Gly Glu Cys
            340                 345
```

<210> SEQ ID NO 23
<211> LENGTH: 1062
<212> TYPE: DNA
<213> ORGANISM: Artificial Sequence
<220> FEATURE:
<223> OTHER INFORMATION: DNA sequence of polypeptide chain H5

<400> SEQUENCE: 23

```
gaggtgcagc tggtggagtc tggaggagga ctggtgcagc caggaggcag cctgaggctg      60
tcttgcgccg cttccggcta caagtatggc gtgtactcca tgggatggtt caggcaggct     120
cctggcaagg gactggaggg cgtgtccgcc atctgttctg cggcagaac cacatactct      180 gactccgtga agggcaggtt taccatctcc cgggataaca gcaaccagat cctgtatctg     240
```

-continued

```
cagatgaact ccctgagagc cgaggacacc gccgtgtact attgcgctgc taggccactg      300
tggacaggcg actgtgatct gtccagctct tggtataaga cctgggggcca gggcaccctg     360 gtgacagtgt ccagcgagag caagtacgga ccaccttgcc caccatgtcc agctcctgag     420
tttgagggag gaccatccgt gttcctgttt cctccaaagc ctaaggacac cctgatgatc      480
agccggacac ctgaggtgac ctgcgtggtg gtggacgtgt ctcaggagga tccagaggtg      540
cagttcaact ggtacgtgga tggcgtggag gtgcacaatg ctaagaccaa gccaagagag      600
gagcagttta attccacata ccgcgtggtg agcgtgctga ccgtgctgca tcaggattgg      660
ctgaacggca aggagtataa gtgcaaggtg tccaataagg ccctgcccag ctctatcgag      720
aagacaatca gcaaggctaa gggacagcct agggagccac aggtgtacac cctgccccct     780
tctcaggagg agatgacaaa gaaccaggtg tccctgacct gtctggtgaa gggcttctat      840
ccaagcgaca tcgctgtgga gtgggagtct aatggccagc ccgagaacaa ttacaagacc      900
acaccacccg tgctggactc tgatggctcc ttctttctgt attctaggct gacagtggat      960
aagtcccggt ggcaggaggg caacgtgttt agctgctctg tgatgcacga ggccctgcac     1020
aatcattata cccagaagtc cctgagcctg tctctgggca ag                        1062
```

<210> SEQ ID NO 24
<211> LENGTH: 354
<212> TYPE: PRT
<213> ORGANISM: Artificial Sequence
<220> FEATURE:
<223> OTHER INFORMATION: Amino acid sequence of polypeptide chain H5

<400> SEQUENCE: 24

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ser Asn Gln Ile Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
            100                 105                 110

Lys Thr Trp Gly Gln Gly Thr Leu Val Thr Val Ser Ser Glu Ser Lys
        115                 120                 125

Tyr Gly Pro Pro Cys Pro Pro Cys Pro Ala Pro Glu Phe Glu Gly Gly
    130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser Gln Glu
                165                 170                 175

Asp Pro Glu Val Gln Phe Asn Trp Tyr Val Asp Gly Val Glu Val His
            180                 185                 190

Asn Ala Lys Thr Lys Pro Arg Glu Glu Gln Phe Asn Ser Thr Tyr Arg
        195                 200                 205

Val Val Ser Val Leu Thr Val Leu His Gln Asp Trp Leu Asn Gly Lys
    210                 215                 220
```

```
Glu Tyr Lys Cys Lys Val Ser Asn Lys Gly Leu Pro Ser Ser Ile Glu
225                 230                 235                 240

Lys Thr Ile Ser Lys Ala Lys Gly Gln Pro Arg Glu Pro Gln Val Tyr
                245                 250                 255

Thr Leu Pro Pro Ser Gln Glu Glu Met Thr Lys Asn Gln Val Ser Leu
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
    290                 295                 300

Leu Asp Ser Asp Gly Ser Phe Phe Leu Tyr Ser Arg Leu Thr Val Asp
305                 310                 315                 320

Lys Ser Arg Trp Gln Glu Gly Asn Val Phe Ser Cys Ser Val Met His
                325                 330                 335

Glu Ala Leu His Asn His Tyr Thr Gln Lys Ser Leu Ser Leu Ser Leu
            340                 345                 350

Gly Lys

<210> SEQ ID NO 25
<211> LENGTH: 45
<212> TYPE: DNA
<213> ORGANISM: Artificial Sequence
<220> FEATURE:
<223> OTHER INFORMATION: DNA sequence of E-linker linker

<400> SEQUENCE: 25
gaacctaagt ctagcgacaa aactcatacc agcccccccta gtcca          45

<210> SEQ ID NO 26
<211> LENGTH: 15
<212> TYPE: PRT
<213> ORGANISM: Artificial Sequence
<220> FEATURE:
<223> OTHER INFORMATION: Amino acid sequence of E-linker linker

<400> SEQUENCE: 26

Glu Pro Lys Ser Ser Asp Lys Thr His Thr Ser Pro Pro Ser Pro
1               5                   10                  15

<210> SEQ ID NO 27
<211> LENGTH: 27
<212> TYPE: DNA
<213> ORGANISM: Artificial Sequence
<220> FEATURE:
<223> OTHER INFORMATION: DNA sequence of G9-linker linker

<400> SEQUENCE: 27
ggtggaggcg gtagtggagg cggttca          27

<210> SEQ ID NO 28
<211> LENGTH: 9
<212> TYPE: PRT
<213> ORGANISM: Artificial Sequence
<220> FEATURE:
<223> OTHER INFORMATION: Amino acid sequence of G9-linker linker

<400> SEQUENCE: 28

Gly Gly Gly Gly Ser Gly Gly Gly Ser
1               5

<210> SEQ ID NO 29
```

-continued

```
<211> LENGTH: 687
<212> TYPE: DNA
<213> ORGANISM: Artificial Sequence
<220> FEATURE:
<223> OTHER INFORMATION: DNA sequence of IgG4 Fc

<400> SEQUENCE: 29
gagagcaagt acggaccacc ttgcccacca tgtccagctc ctgagtttga gggaggacca        60
tccgtgttcc tgtttcctcc aaagcctaag gacaccctga tgatcagccg gacacctgag       120
gtgacctgcg tggtggtgga cgtgtctcag gaggatccag aggtgcagtt caactggtac       180
gtggatggcg tggaggtgca caatgctaag accaagccaa gagaggagca gtttaattcc       240
acataccgcg tggtgagcgt gctgaccgtg ctgcatcagg attggctgaa cggcaaggag       300
tataagtgca aggtgtccaa taagggcctg cccagctcta tcgagaagac aatcagcaag       360
gctaagggac agcctaggga gccacaggtg tacaccctgc ccccttctca ggaggagatg       420
acaaagaacc aggtgtccct gacctgtctg gtgaagggct ctatccaag cgacatcgct        480 gtggagtggg agtctaatgg ccagcccgag aacaattaca gaccacacc acccgtgctg        540 gactctgatg gctccttctt tctgtattct aggctgacag tggataagtc ccggtggcag       600
gagggcaacg tgtttagctg ctctgtgatg cacgaggccc tgcacaatca ttatacccag       660
aagtccctga gcctgtctct gggcaag                                           687

<210> SEQ ID NO 30
<211> LENGTH: 229
<212> TYPE: PRT
<213> ORGANISM: Artificial Sequence
<220> FEATURE:
<223> OTHER INFORMATION: Amino acid sequence of IgG4 Fc

<400> SEQUENCE: 30

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
```

-continued

```
            195                 200                 205
Val Met His Glu Ala Leu His Asn His Tyr Thr Gln Lys Ser Leu Ser
    210                 215                 220

Leu Ser Leu Gly Lys
225

<210> SEQ ID NO 31
<211> LENGTH: 10
<212> TYPE: PRT
<213> ORGANISM: Artificial Sequence
<220> FEATURE:
<223> OTHER INFORMATION: CDR1 sequence of a heavy chain of anti-CD47
      antibody

<400> SEQUENCE: 31

Gly Tyr Ser Phe Thr His His Trp Ile His
1               5                   10

<210> SEQ ID NO 32
<211> LENGTH: 17
<212> TYPE: PRT
<213> ORGANISM: Artificial Sequence
<220> FEATURE:
<223> OTHER INFORMATION: CDR2 sequence of a heavy chain of anti-CD47
      antibody

<400> SEQUENCE: 32

Met Ile Asp Ala Ser Asp Ser Glu Thr Arg Leu Ser Gln Lys Phe Lys
1               5                   10                  15

Asp

<210> SEQ ID NO 33
<211> LENGTH: 8
<212> TYPE: PRT
<213> ORGANISM: Artificial Sequence
<220> FEATURE:
<223> OTHER INFORMATION: CDR3 sequence of a heavy chain of anti-CD47
      antibody

<400> SEQUENCE: 33

Leu Gly Arg Tyr Tyr Phe Asp Tyr
1               5

<210> SEQ ID NO 34
<211> LENGTH: 11
<212> TYPE: PRT
<213> ORGANISM: Artificial Sequence
<220> FEATURE:
<223> OTHER INFORMATION: CDR1 sequence of a light chain of anti-CD47
      antibody

<400> SEQUENCE: 34

Arg Ala Ser Glu Asn Val Gly Thr Tyr Ile Ser
1               5                   10

<210> SEQ ID NO 35
<211> LENGTH: 7
<212> TYPE: PRT
<213> ORGANISM: Artificial Sequence
<220> FEATURE:
<223> OTHER INFORMATION: CDR2 sequence of a light chain of anti-CD47
      antibody

<400> SEQUENCE: 35

Gly Ala Ser Asn Arg Tyr Thr
1               5
```

<210> SEQ ID NO 36
<211> LENGTH: 9
<212> TYPE: PRT
<213> ORGANISM: Artificial Sequence
<220> FEATURE:
<223> OTHER INFORMATION: CDR3 sequence of a light chain of anti-CD47
      antibody

<400> SEQUENCE: 36

Gly Glu Ser Tyr Gly His Leu Tyr Thr
1               5

<210> SEQ ID NO 37
<211> LENGTH: 375
<212> TYPE: DNA
<213> ORGANISM: Artificial Sequence
<220> FEATURE:
<223> OTHER INFORMATION: DNA sequence of a TIGIT single domain antibody

<400> SEQUENCE: 37
gaggtgcagc tggtggagtc tggaggagga ctggtgcagc caggaggcag cctgaggctg        60
tcttgcgccg cttccggcta caagtatggc gtgtactcca tgggatggtt caggcaggct       120
cctggcaagg gactggaggg cgtgtccgcc atctgttctg gcggcagaac cacatactct       180
gactccgtga agggcaggtt taccatctcc cgggataaca gcaaccagat cctgtatctg       240
cagatgaact ccctgagagc cgaggacacc gccgtgtact attgcgctgc taggccactg       300
tggacaggcg actgtgatct gtccagctct tggtataaga cctggggcca gggcaccctg       360
gtgacagtgt ccagc                                                         375

<210> SEQ ID NO 38
<211> LENGTH: 125
<212> TYPE: PRT
<213> ORGANISM: Artificial Sequence
<220> FEATURE:
<223> OTHER INFORMATION: Amino acid sequence of a TIGIT single domain
      antibody

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Lys Tyr Gly Val Tyr
            20                  25                  30

Ser Met Gly Trp Phe Arg Gln Ala Pro Gly Lys Gly Leu Glu Gly Val
        35                  40                  45

Ser Ala Ile Cys Ser Gly Gly Arg Thr Thr Tyr Ser Asp Ser Val Lys
    50                  55                  60

Gly Arg Phe Thr Ile Ser Arg Asp Asn Ser Asn Gln Ile Leu Tyr Leu
65                  70                  75                  80

Gln Met Asn Ser Leu Arg Ala Glu Asp Thr Ala Val Tyr Tyr Cys Ala
                85                  90                  95

Ala Arg Pro Leu Trp Thr Gly Asp Cys Asp Leu Ser Ser Ser Trp Tyr
            100                 105                 110

Lys Thr Trp Gly Gln Gly Thr Leu Val Thr Val Ser Ser
        115                 120                 125

<210> SEQ ID NO 39
<211> LENGTH: 10
<212> TYPE: PRT
<213> ORGANISM: Artificial Sequence -continued

```
<220> FEATURE:
<223> OTHER INFORMATION: Amino acid sequence of CDR1 of a TIGIT single
      domain antibody

<400> SEQUENCE: 39

Gly Tyr Lys Tyr Gly Val Tyr Ser Met Gly
1               5                   10

<210> SEQ ID NO 40
<211> LENGTH: 16
<212> TYPE: PRT
<213> ORGANISM: Artificial Sequence
<220> FEATURE:
<223> OTHER INFORMATION: Amino acid sequence of CDR2 of a TIGIT single
      domain antibody

<400> SEQUENCE: 40

Ala Ile Cys Ser Gly Gly Arg Thr Thr Tyr Ser Asp Ser Val Lys Gly
1               5                   10                  15

<210> SEQ ID NO 41
<211> LENGTH: 17
<212> TYPE: PRT
<213> ORGANISM: Artificial Sequence
<220> FEATURE:
<223> OTHER INFORMATION: Amino acid sequence of CDR3 of a TIGIT single
      domain antibody

<400> SEQUENCE: 41

Arg Pro Leu Trp Thr Gly Asp Cys Asp Leu Ser Ser Ser Trp Tyr Lys
1               5                   10                  15

Thr
```

ANTI-CD47/ANTI-TIGIT BISPECIFIC ANTIBODY, PREPARATION METHOD THEREFOR AND APPLICATION THEREOF

CROSS REFERENCE TO RELATED APPLICATIONS

This is the U.S. National Stage of International Application No. PCT/CN2020/097924, filed Jun. 24, 2020, which was published in Chinese under PCT Article 21(2), which in turn claims the benefit of Chinese Patent Application No. 201910554742.1, filed Jun. 25, 2019.

INCORPORATION OF ELECTRONIC SEQUENCE LISTING

The present application contains a Sequence Listing, which is submitted as an ASCII text file, named "P10448-PI-US.250618. Amended Sequence Listing.txt," 143,512 bytes, and created on Jun. 9, 2025, which is incorporated herein by reference.

TECHNICAL FIELD

The present invention belongs to the field of antibodies, and specifically relates to bispecific antibodies and a preparation method and an application thereof. The bispecific antibodies include a first antigen binding portion that specifically binds to CD47, and a second antigen binding portion that specifically binds to TIGIT.

BACKGROUND

The mammalian immune system is a host defense system that protects against microbial infections and prevents carcinogenesis (Chen et al., Frontiers Immunol. 9:320 (2018)). The immune system is spread all over the body, which is an extremely complex network system composed of different immune cells, and specific tissues and organs exerting a synergistic effect. When the immune system is functioning normally, the diseased cells in the host body will be recognized and eliminated from the healthy cells, thus ensuring the stability of the environment in the body. Therefore, maintaining the integrity of the immune system is essential to maintaining our own health. Conversely, losing control of the immune system can lead to autoimmune diseases, inflammation, cancer and the like (Ribas et al., Cancer Discovery 5:915-9 (2015); Yao and Chen, Eur. J. Immunol. 43:576-9 (2013)). The immune system can be divided into two categories, namely humoral immunity and cell-mediated immunity. Antibodies and other biological macromolecules regulate the humoral immunity. In contrast, the regulation of cellular immunity is achieved at the cellular level, involving the activation of macrophages, natural killer cells and antigen-specific killer T cells.

Activation and suppression of immune response are mainly regulated by two independent signaling pathways (Gorentla and Zhong, J. Clin. Cell. Immunol. (2012); Huse, J. Cell Sci. 122:1269-73 (2009); Mizota et al., J. Anesthesia 27:80-7 (2013)). The first signal is mediated by an antigen. When the T cell receptor specifically recognizes and binds to the antigen peptide presented by the MHC on the surface of the antigen presenting cells (APC), the first signal is generated. The second signal is provided by the interaction between antigen presenting cells and co-stimulatory molecules expressed on the surface of T cells. When the first and second signals are activated in sequence, the tumors can be killed by T cells. If the second signal is in lack, T cells will enter an unresponsive state or immune tolerance, and even cause programmed cell death.

As mentioned above, the second signaling pathway is very important for activating immune cells. Specifically, co-stimulatory and co-inhibitory receptors participate in the second signaling pathway, induce immune response and regulation of antigen-receptor presentation, balance positive and negative signals while maintaining immune tolerance of autoantigens, and maximize the immune response to invaders (Chen and Flies, Nat. Rev. Immunol. 13:227-42 (2013); Ewing et al., Int. J. Cardiol. 168:1965-74 (2013); Liu et al., Immunol. Invest. 45:813-31 (2016); Shen et al., Frontiers in Biosci. 24:96-132 (2019); Zhang and Vignali, Immunity 44:1034-51(2016)).

TIGIT, known as T cell immunoglobulin and ITIM domain protein, is an inhibitory receptor containing Ig and ITIM domains shared by T cells and NK cells. TIGIT is highly expressed in T cells and natural killer (NK) cells. TIGIT, CD96, CD226 and related ligands together form an immunomodulatory signaling pathway. Similar to the CD28/CTLA-4 signaling pathway, the CD226/TIGIT/CD96 signaling pathway also contains co-stimulatory receptors and co-inhibitory receptors sharing some or all of the ligands, in which CD226 is a co-stimulatory receptor and delivers stimulus signals upon combining with ligands, and TIGIT and CD96 are co-inhibitory receptors and deliver inhibitory signals upon combining with related ligands. TIGIT has two ligands, i.e. CD155 and CD122, which are also ligands of CD226. These two ligands are expressed in APC cells, T cells and tumor cells. The ligands of CD96 include CD155 and CD111. The affinity of TIGIT with the ligand CD155 is significantly higher than that of TIGIT with the ligand CD122, and also significantly higher than the affinity of CD226 or CD96 with the ligand CD155. Similar to PD-1 and CTLA-4 receptors, TIGIT is also an important inhibitory immune receptor. Inhibition of TIGIT can promote the proliferation and function of T cells; blockade of TIGIT can also enhance the anti-tumor immune response mediated by NK cells, thereby inhibiting tumor growth. Therefore, monoclonal antibodies targeting the inhibitory receptor TIGIT can significantly enhance the effect of tumor immunotherapy.

CD47, also known as an integrin-associated protein, is a transmembrane protein encoded by the CD47 gene and belongs to the immunoglobulin superfamily. CD47 is widely expressed on the surface of normal cells and can interact with signal regulatory protein α (SIRP α), thrombospondin (TSP1) and integrin to mediate cell apoptosis, proliferation, immune responses, and the like. CD47 is an innate immune checkpoint receptor, which releases a "don't eat me" signal to macrophages, inhibits phagocytosis, and thus avoids being attacked by the body's immune system upon binding to SIRPα mainly expressed on macrophage nucleus and dendritic cells. Cancer cells prevent phagocytosis by up-regulating the expression of CD47, thereby evading immune surveillance. CD47 is overexpressed in blood and solid tumors, which is highly correlated with the poor prognosis of clinical treatment. Therefore, the use of anti-CD47 antibodies or high-affinity SIRPα variants to block the CD47-SIRPα signaling pathway has become a potential strategy to promote the phagocytosis of tumor cells by macrophages. However, given the widespread expression of CD47, anti-CD47 antibodies have a high risk of binding to healthy cells, especially red blood cells, and increasing the risk of blood toxicity. At the same time, more and more studies have shown that blocking CD47 alone is not sufficient to generate anti-tumor immunity in immunocompetent hosts. In addition, researchers at Stanford University reported that SIRPα treatment that interferes with the CD47/SIRPα pathway does not induce phagocytosis (Sockolosky et al., PNAS 113:E2646-2654 (2016)). Therefore, considering the effectiveness and safety of cancer treatment, anti-CD47 antibodies need to be further optimized to improve tumor targeting specificity.

SUMMARY

In one aspect, the present invention provides an isolated bispecific binding protein including a first antigen binding portion that specifically binds CD47 and a second antigen binding portion that specifically binds TIGIT. Specifically, the present invention provides an isolated anti-CD47/anti-TIGIT bispecific antigen binding protein or a fragment thereof including (a) a first antigen binding portion including a heavy chain variable region ($V_H$) and a light chain variable region ($V_L$), with $V_H$ and $V_L$ forming an antigen binding site that specifically binds to CD47; and (b) a second antigen binding portion including a single domain antibody (sdAb) that specifically binds to TIGIT, where the first antigen binding portion and the second antigen binding portion are fused to each other.

In some embodiments, the $V_H$ of the first antigen binding portion includes the heavy chain complementarity determining regions HCDR1, HCDR2, and HCDR3, and the amino acid sequences of the HCDR1, HCDR2, and HCDR3 are as shown in SEQ ID NO:31, SEQ ID NO:32 and SEQ ID NO:33, respectively, or the sequence as shown contains up to three (3, 2 or 1) amino acid mutations, respectively; the $V_L$ of the first antigen binding portion includes the light chain complementarity determining regions LCDR1, LCDR2 and LCDR3, and the amino acid sequences of the LCDR1, LCDR2, and LCDR3 are as shown in SEQ ID NO:34, SEQ ID NO:35 and SEQ ID NO:36, respectively, or the sequence as shown contains up to three (3, 2 or 1) amino acid mutations, respectively. In some embodiments, the $V_H$ of the first antigen binding portion includes the heavy chain complementarity determining regions HCDR1, HCDR2, and HCDR3, and the amino acid sequences of the HCDR1, HCDR2, and HCDR3 are as shown in SEQ ID NO:31, SEQ ID NO:32 and SEQ ID NO:33, respectively or the sequence as shown contains up to three (3, 2 or 1) amino acid substitutions, respectively; the $V_L$ of the first antigen binding portion includes the light chain complementarity determining regions LCDR1, LCDR2 and LCDR3, and the amino acid sequences of the LCDR1, LCDR2, and LCDR3 are as shown in SEQ ID NO:34, SEQ ID NO:35 and SEQ ID NO:36, respectively, or the sequence as shown contains up to three (3, 2 or 1) amino acid substitutions, respectively. In some specific embodiments, the $V_H$ of the first antigen binding portion includes the heavy chain complementarity determining regions HCDR1, HCDR2, and HCDR3, and the amino acid sequences of the HCDR1, HCDR2, and HCDR3 are as shown in SEQ ID NO:31, SEQ ID NO:32 and SEQ ID NO:33, respectively; the $V_L$ of the first antigen binding portion includes the light chain complementarity determining regions LCDR1, LCDR2, and LCDR3, and the amino acid sequences of LCDR1, LCDR2, and LCDR3 are as shown in SEQ ID NO:34, SEQ ID NO:35 and SEQ ID NO:36, respectively.

In some embodiments, the single domain antibody of the second antigen binding portion includes the complementarity determining regions CDR1, CDR2, and CDR3, and the amino acid sequences of the CDR1, CDR2, and CDR3 are as shown in SEQ ID NO:39, SEQ ID NO:40, and SEQ ID NO:41, respectively, or the sequence as shown contains up to three (3, 2 or 1) amino acid mutations, respectively. In some embodiments, the single domain antibody of the second antigen binding portion includes the complementarity determining regions CDR1, CDR2, and CDR3, and the amino acid sequences of the CDR1, CDR2, and CDR3 are as shown in SEQ ID NO:39, SEQ ID NO:40, and SEQ ID NO:41, respectively, or the sequence as shown contains up to three (3, 2 or 1) amino acid substitutions, respectively. In some specific embodiments, the single domain antibody of the second antigen binding portion includes the complementarity determining regions CDR1, CDR2 and CDR3, and the amino acid sequences of the CDR1, CDR2 and CDR3 are as shown in SEQ ID NO:39, SEQ ID NO:40 and SEQ ID NO:41, respectively.

In some embodiments, the first antigen binding portion is a full-length antibody, including two heavy chains including $V_H$ and two light chains including $V_L$.

In some embodiments, the first antigen binding portion and the second antigen binding portion are fused. In some specific embodiments, the C-terminus of the second antigen binding portion is fused to the N-terminus of at least one heavy chain of the first antigen binding portion or the N-terminus of at least one light chain of the first antigen binding portion. In some embodiments, the N-terminus of the second antigen binding portion is fused to the C-terminus of at least one heavy chain of the first antigen binding portion or the C-terminus of at least one light chain of the first antigen binding portion.

In some embodiments, the first antigen binding portion and the second antigen binding portion are fused via a peptide bond or a peptide linker. In some embodiments, the peptide linker is selected from a mutated human IgG1 hinge region or a GS linker. In some preferred embodiments, the amino acid sequence of the peptide linker is as shown in SEQ ID NO:26 or SEQ ID NO:28.

In some embodiments, the heavy chain of the first antigen binding portion includes a sequence having at least 80%, 85%, 90%, 95%, 96%, 97%, 98% or 99% identity with the amino acid sequence shown in SEQ ID NO:4, and the light chain of the first antigen binding portion includes a sequence having at least 80%, 85%, 90%, 95%, 96%, 97%, 98% or 99% identity with the amino acid sequence shown in SEQ ID NO:6. In some embodiments, the heavy chain of the first antigen binding portion includes a sequence having at least 95% identity with the amino acid sequence shown in SEQ ID NO:4, and the light chain of the first antigen binding portion includes a sequence having at least 95% identity with the amino acid sequence shown in SEQ ID NO:6. In some specific embodiments, the heavy chain of the first antigen binding portion includes the amino acid sequence shown in SEQ ID NO:4, and the light chain of the first antigen binding portion includes the amino acid sequence shown in SEQ ID NO:6.

In some embodiments, the second antigen binding portion includes a sequence having at least 80%, 85%, 90%, 95%, 96%, 97%, 98% or 99% identity with the amino acid sequence shown in SEQ ID NO:38. In some embodiments, the second antigen binding portion includes a sequence having at least 95% identity with the amino acid sequence shown in SEQ ID NO:38. In some specific embodiments, the second antigen binding portion includes the amino acid sequence shown in SEQ ID NO:38.

In some embodiments, an isolated anti-CD47/anti-TIGIT bispecific antigen binding protein or a fragment thereof is provided, in which the heavy chain of the first antigen binding portion includes a sequence having at least 80%, 85%, 90%, 95%, 96%, 97%, 98% or 99% identity with the amino acid sequence shown in SEQ ID NO:4, and the light chain of the first antigen binding portion includes a sequence having at least 80%, 85%, 90%, 95%, 96%, 97%, 98% or 99% identity with the amino acid sequence shown in SEQ ID NO:6; and the second antigen binding portion includes a sequence having at least 80%, 85%, 90%, 95%, 96%, 97%, 98% or 99% identity with the amino acid sequence shown in SEQ ID NO:38. In some specific embodiments, in the isolated anti-CD47/anti-TIGIT bispecific antigen binding protein or a fragment thereof, the heavy chain of the first antigen binding portion includes the amino acid sequence shown in SEQ ID NO:4, and the light chain of the first antigen binding portion includes the amino acid sequence shown in SEQ ID NO:6; and the second antigen binding portion includes the amino acid sequence shown in SEQ ID NO:38.

In some embodiments, the first antigen binding portion includes a human, humanized or chimeric antibody or a fragment thereof. In some embodiments, the second antigen binding portion includes a single domain antibody that specifically binds to TIGIT, which is camelid, chimeric, humanized, or human.

In some embodiments, an isolated anti-CD47/anti-TIGIT bispecific antigen binding protein or a fragment thereof including an anti-CD47 antibody and an anti-TIGIT single domain antibody is provided, in which the N-terminus of the anti-TIGIT single domain antibody is fused to the C-terminus of the two heavy chains of the anti-CD47 antibody, where a heavy chain fusion polypeptide includes a sequence having at least 80%, 85%, 90%, 95%, 96%, 97%, 98% or 99% identity with the amino acid sequence shown in SEQ ID NO:8 or SEQ ID NO:12, and a light chain polypeptide includes a sequence having at least 80%, 85%, 90%, 95%, 96%, 97%, 98% or 99% identity with the amino acid sequence shown in SEQ ID NO:6. In some specific embodiments, the isolated anti-CD47/anti-TIGIT bispecific antigen binding protein or a fragment thereof includes an anti-CD47 antibody and an anti-TIGIT single domain antibody, and the N-terminus of the anti-TIGIT single domain antibody is fused to the C-terminus of the two heavy chains of the anti-CD47 antibody, where the heavy chain fusion polypeptide includes the amino acid sequence shown in SEQ ID NO:8 or SEQ ID NO:12, and the light chain polypeptide includes the amino acid sequence shown in SEQ ID NO:6.

In some embodiments, another isolated anti-CD47/anti-TIGIT bispecific antigen binding protein or a fragment thereof including an anti-CD47 antibody and an anti-TIGIT single domain antibody is provided, in which the C-terminus of the anti-TIGIT single domain antibody is fused to the N-terminus of the two heavy chains of the anti-CD47 antibody, where the heavy chain fusion polypeptide includes a sequence having at least 80%, 85%, 90%, 95%, 96%, 97%, 98% or 99% identity with the amino acid sequence shown in SEQ ID NO:10 or SEQ ID NO:14, and the light chain polypeptide includes a sequence having at least 80%, 85%, 90%, 95%, 96%, 97%, 98% or 99% identity with the amino acid sequence shown in SEQ ID NO:6. In some specific embodiments, the isolated anti-CD47/anti-TIGIT bispecific antigen binding protein or a fragment thereof includes an anti-CD47 antibody and an anti-TIGIT single domain antibody, and the C-terminus of the anti-TIGIT single domain antibody is fused to the N-terminus of the two heavy chains of the anti-CD47 antibody, where the heavy chain fusion polypeptide includes the amino acid sequence shown in SEQ ID NO:10 or SEQ ID NO:14, and the light chain polypeptide includes the amino acid sequence shown in SEQ ID NO:6.

In some embodiments, an isolated anti-CD47/anti-TIGIT bispecific antigen binding protein or a fragment thereof including an anti-CD47 antibody and an anti-TIGIT single domain antibody is provided, in which the N-terminus of the anti-TIGIT single domain antibody is fused to the C-terminus of the two light chains of the anti-CD47 antibody, where a light chain fusion polypeptide includes a sequence having at least 80%, 85%, 90%, 95%, 96%, 97%, 98% or 99% identity with the amino acid sequence shown in SEQ ID NO:16 or SEQ ID NO:20, and a heavy chain polypeptide includes a sequence having at least 80%, 85%, 90%, 95%, 96%, 97%, 98% or 99% identity with the amino acid sequence shown in SEQ ID NO:4. In some specific embodiments, the isolated anti-CD47/anti-TIGIT bispecific antigen binding protein or a fragment thereof includes an anti-CD47 antibody and an anti-TIGIT single domain antibody, and the N-terminus of the anti-TIGIT single domain antibody is fused to the C-terminus of the two light chains of the anti-CD47 antibody, where the light chain fusion polypeptide includes the amino acid sequence shown in SEQ ID NO:16 or SEQ ID NO:20, and the heavy chain polypeptide includes the amino acid sequence shown in SEQ ID NO:4.

In some embodiments, another isolated anti-CD47/anti-TIGIT bispecific antigen binding protein or a fragment thereof including an anti-CD47 antibody and an anti-TIGIT single domain antibody is provided, in which the C-terminus of the anti-TIGIT single domain antibody is fused to the N-terminus of the two light chains of the anti-CD47 antibody, where the light chain fusion polypeptide includes a sequence having at least 80%, 85%, 90%, 95%, 96%, 97%, 98% or 99% identity with the amino acid sequence shown in SEQ ID NO:18 or SEQ ID NO:22, and the heavy chain polypeptide includes a sequence having at least 80%, 85%, 90%, 95%, 96%, 97%, 98% or 99% identity with the amino acid sequence shown in SEQ ID NO:4. In some specific embodiments, the isolated anti-CD47/anti-TIGIT bispecific antigen binding protein or a fragment thereof includes an anti-CD47 antibody and an anti-TIGIT single domain antibody, and the C-terminus of the anti-TIGIT single domain antibody is fused to the N-terminus of the two light chains of the anti-CD47 antibody, where the light chain fusion polypeptide includes the amino acid sequence shown in SEQ ID NO:18 or SEQ ID NO:22, and the heavy chain polypeptide includes the amino acid sequence shown in SEQ ID NO:4.

In another aspect, the present invention provides an isolated polynucleotide encoding the anti-CD47/anti-TIGIT bispecific antigen binding protein or a fragment thereof as described above. It is well known to those skilled in the art that the change (for example, substitution and deletion) in the sequence of the encoded protein will not change the amino acid of the protein.

Further, a vector containing the isolated polynucleotide encoding the isolated anti-CD47/anti-TIGIT bispecific antigen binding protein or a fragment thereof as described above is provided. The vector is well known to those skilled in the art, such as plasmids, phage vectors or viral vectors. In some specific embodiments, the vector is a recombinant expression vector, such as a plasmid. These vectors include arbitrary elements to support their functions as conventional expression vectors, such as promoters, ribosome binding elements, terminator, enhancers, selectable markers, and origins of replication. Among them, the promoter can be a conventional promoter, an inducible promoter or a repressible promoter. It is well known in the art that many expression vectors are able to deliver nucleic acids into cells, and can be used to produce antibodies or antigen-binding fragments thereof in the cells. According to the methods in the examples of the present invention, conventional cloning techniques or artificial gene synthesis can be used to produce recombinant expression vectors.

Further, a host cell containing the isolated polynucleotide or vector as described above is provided. In the present invention, any host cell conventional in the art can be used for the expression of antibodies or antigen-binding frag- ments thereof. In some embodiments, the host cell is *E. coli* TG1 or BL21 (for the expression of antibodies such as scFv or Fab), CHO-DG44, CHO-3E7, CHO-K1 or HEK293. According to specific examples, the recombinant expression vector is transfected into host cells by conventional methods (such as chemical transfection, thermal transfection, or electrotransfection), and stably integrated into the host cell genome, so that the recombinant nucleic acid can be effec- tively expressed.

In another aspect, the present invention provides a method for producing an isolated anti-CD47/anti-TIGIT bispecific antigen binding protein or a fragment thereof, which includes culturing a host cell containing a polynucleotide encoding the bispecific antigen binding protein or a frag- ment thereof according to the present invention under suit- able conditions and recovering the antibody or fragments thereof from cells or cell culture fluid. The expressed antibody or a fragment thereof can be obtained from cells or extracted and purified by conventional methods in the art.

In another aspect, the present invention provides a phar- maceutical composition including the isolated anti-CD47/ anti-TIGIT bispecific antigen binding protein or a fragment thereof as described above and a pharmaceutically accept- able carrier. The "pharmaceutically acceptable carrier" refers to substances such as solid or liquid diluents, fillers, antioxidants and stabilizers that can be administered safely, suitable for administration to human and/or animal without excessive adverse side effects, and also suitable for main- taining the vitality of the medications or active agents therein. Depending to the route of administration, various carriers well known in the art can be administered, including but not limited to, sugar, starch, cellulose and its derivative, maltose, gelatin, talc, calcium sulfate, vegetable oil, syn- thetic oil, polyol, alginic acid, phosphate buffer, emulsifier, isotonic saline, and/or pyrogen-free water. The pharmaceu- tical composition provided by the present invention can be formulated into clinically acceptable dosage forms such as powders and injections. The pharmaceutical composition according to the present invention can be administered to the subject by any appropriate route, for example, oral, intra- venous infusion, intramuscular injection, subcutaneous injection, subperitoneal, rectal, sublingual, or via inhalation and transdermal.

In another aspect, the present invention provides a method for treating a subject suffering from or at risk of suffering from a disease associated with abnormal expression of CD47 and/or TIGIT, including administering to the subject an effective amount of any of the pharmaceutical composi- tions as described above.

In another aspect, the present invention provides the application of the anti-CD47/anti-TIGIT bispecific antigen binding protein or fragments, polynucleotides, vectors, and host cells thereof in the preparation of medications for a disease associated with abnormal expression of CD47 and/or TIGIT.

In some embodiments, the disease associated with CD47 and/or TIGIT is cancer. In some embodiments, the cancer is a solid tumor, such as rectal cancer, non-small cell lung cancer, small cell lung cancer, renal cell cancer, ovarian cancer, breast cancer, pancreatic cancer, gastric cancer, bladder cancer, esophageal cancer, mesothelioma, mela- noma and head and neck cancer. In a preferred embodiment, the cancer is a solid tumor, such as pancreatic cancer, non-small cell lung cancer, ovarian cancer, melanoma, breast cancer, gastric cancer, colorectal cancer, prostate cancer, and uterine cancer.

In some embodiments, the above method further includes administering additional tumor therapies to the individual, such as surgery, radiation therapy, chemotherapy, immuno- therapy, hormone therapy, or a combination thereof.

In the present invention, the TIGIT single domain anti- body is connected to the terminus of the heavy or light chain of the anti-CD47 monoclonal antibody in a specific connec- tion manner, and the resulting anti-CD47/anti-TIGIT bispe- cific antigen binding protein has a significantly increased affinity for the TIGIT antigen.

At the same time, the biological activity of this bispecific antibody for blocking TIGIT is also significantly enhanced, which shows that the increased affinity of the bispecific antibody to TIGIT antigen can enhance the corresponding biological activity. At the same time, this bispecific antibody can also block the CD47 signaling pathway, so that it can block two modes of tumor immune escape simultaneously.

Term Interpretation

"fragment of antigen binding protein" means antibody fragments and antibody analogs, which usually include at least part of the antigen binding region or variable region (for example, one or more CDRs) of a parental antibody. Antibody fragments retain at least some of the binding specificity of the parental antibody. For example, the frag- ments of antigen binding protein capable of binding to CD47 or a portion thereof include but not limited to sdAb (single domain antibody), Fab (for example, the antibody obtained by papain digestion), $F(ab')_2$ (for example, obtained by pepsin digestion), Fv or scFv (for example, obtained by molecular biology techniques).

"single domain antibody (sdAb)" refers to a single antigen binding polypeptide with three complementarity deter- mining regions (CDRs). These single domain antibod- ies can bind to antigen alone without pairing with corresponding CDR-containing polypeptides. In some cases, single domain antibodies are artificially engi- neered from camel heavy chain antibodies and are called "$V_H H$ segments". Cartilaginous fish also has heavy chain antibodies (IgNAR, the abbreviation of immunoglobulin new antigen receptor), from which single domain antibodies called "$V_{NAR}$ segments" can also be produced. Camelidae sdAb is the smallest well-known antigen binding antibody fragment (see, e.g., Hamers-Casterman et al., Nature 363:446-8 (1993); Greenberg et al., Nature 374:168-73 (1995); Hassanzadeh-Ghassabeh et al., Nanomedicine (Lond), 8:1013-26 (2013)). The basic $V_H H$ has the following structure from N-terminus to C-terminus: FR1-CDR1- FR2-CDR2-FR3-CDR3-FR4, where FR1 to FR4 are framework regions 1 to 4, respectively, and CDR1 to CDR3 refer to complementarity determining regions 1 to 3. The anti-TIGIT single domain antibody involved in the present invention refers to a single domain antibody that can specifically bind to TIGIT, especially a single domain antibody that binds to human TIGIT. The anti-TIGIT single domain antibody according to the present invention can be selected from the anti- TIGIT single domain antibody specifically described in the patent application PCT/CN2018/124979. For the construction, expression, extraction and purification methods of the anti-TIGIT single domain antibody according to the present invention, please refer to the patent application PCT/CN2018/124979.

"full-length antibody" refers to an antibody having four full-length chains, including a heavy chain and a light chain containing an Fc region. The anti-CD47 antibody involved in the present invention refers to an antibody that can specifically bind to CD47, especially an antibody that binds to human CD47. The anti-CD47 antibody according to the present invention can be selected from the anti-CD47 antibodies specifically described in PCT/CN2019/072929. For the construction, expression, extraction and purification methods of the anti-CD47 antibody according to the present invention, please refer to the patent application PCT/CN2019/072929.

"mutation" refers to a polypeptide in which an antigen binding protein or protein fragment contains the change in one or more (several) amino acid residues at one or more (several) positions, that is, a polypeptide that is substituted, inserted, and/or deleted. Substitution refers to the replacement of an amino acid occupying a certain position with a different amino acid; deletion refers to the removal of an amino acid occupying a certain position; and insertion refers to the addition of 1-5 amino acids adjacent to and after the amino acid occupying a certain position.

"amino acid sequence identity" is defined as the percentage of amino acid residues in a candidate sequence that are identical to amino acid residues in a particular peptide or polypeptide sequence obtained by aligning sequences and introducing gaps when necessary to obtain the maximum percent sequence identity without considering any conservative substitutions as portion of the sequence identity. Sequence alignment can be performed in a variety of ways within the skill of the art to determine percent amino acid sequence identity, for example, using publicly available computer software, such as BLAST, BLAST-2, ALIGN, or Megalign (DNASTAR) software. Those skilled in the art can determine the appropriate parameters for measuring the alignment, including any algorithm required to obtain the maximum alignment over the entire length of the sequence being aligned.

"GS linker" refers to the GS combination of glycine (G) and serine (S), which is used to bind multiple proteins together to form a fusion protein. The commonly used GS combination is (GGGGS)n (SEQ ID NO: 42), and the length of the linker sequence is changed by changing the value of n. Among them, most GS combinations adopt (GGGGS)3 (SEQ ID NO: 43). At the same time, glycine and serine can also generate different linker sequences by means of other combinations, such as the G9-linker used in the present invention, and the GS combination is GGGGSGGGS (SEQ ID NO: 28).

DETAILED DESCRIPTION

Figure 1:
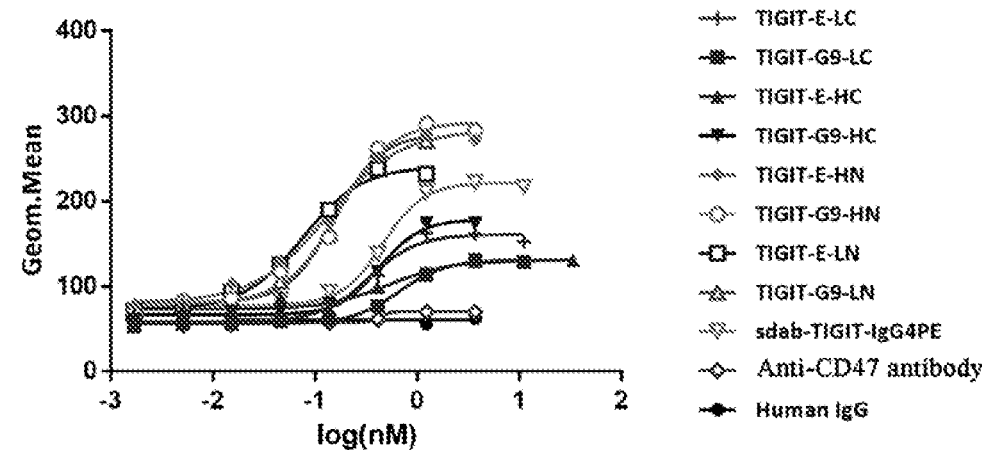
FIG. 1 Affinity between samples and TIGIT-expressing CHO-K1 cells determined by flow cytometry FIG. 2 Affinity between samples and CD47-expressing CHO-K1 cells determined by flow cytometry FIG. 3 TIGIT blocking activity of samples determined by the TIGIT/CD155 blocking bioassay system FIG. 4 Activity of the bispecific antibody TIGIT-G9-HN determined by the cell phagocytosis test of anti-CD47 antibody

The present invention is described in detail below with reference to specific implementations. It should be understood that the implementations are merely intended to describe the present invention rather than to limit the scope of the present invention. In addition, it should be understood that, after reading the teaching of the present invention, those skilled in the art can make various changes or modifications to the present invention, and these equivalent forms also fall within the scope defined by the appended claims of this application. Unless otherwise specified, the methods and materials in the examples described below are commercially available and conventional products.

Example 1 Construction and Expression of Anti-CD47/Anti-TIGIT Bispecific Antibodies A series of anti-CD47/anti-TIGIT bispecific antibodies were designed using an anti-CD47 monoclonal antibody (mAb) and a TIGIT single domain antibody (sdAb) respectively. The sequences of the two antibodies are shown in Table 1 and Table 2.

The TIGIT single domain antibody was fused to the N-terminus or C-terminus of the heavy or light chain of the anti-CD47 monoclonal antibody through two linker sequences (E-linker: EPKSSDKTHTSPPSP (SEQ ID NO: 26) or G9-linker: GGGGSGGGS (SEQ ID NO: 28)). Each bispecific antibody structure was composed of two identical fusion polypeptide chains and two identical natural polypeptide chains, and the DNA sequence expressing each polypeptide chain was inserted into the pTT5 vector between the EcoRI and HindIII restriction sites. Each plasmid also included a secretion signal sequence for the protein secreted into the growth medium. The TIGIT single domain antibody was fused to the N-terminus of the IgG4-Fc portion with site mutations (S228P and L235E) as a control for biological activity assay in vitro. The plasmids expressing the bispecific antibody protein are shown in Table 3.

TABLE 1

DNA and amino acid sequences of anti-CD47 monoclonal antibodies

| DNA sequence | | SEQ ID NO: |
|---|---|---|
| DNA sequence of a heavy chain of anti-CD47 antibody | GAGGTGCAGCTGGTGCAGTCCGGAGCTGAGGTGAAGAAG CCAGGATCCAGCGTGAAGGTGAGCTGCAAGGCTAGCGGC TACTCTTTCACCCACCATTGGATCCACTGGGTGAGGCAG GCTCCTGGACAGGGACTGGAGTGGATGGGCATGATCGAC GCTTCCGATAGCGAGACAAGACTGTCTCAGAAGTTTAAG | 3 |

TABLE 1-continued

DNA and amino acid sequences of anti-CD47
monoclonal antibodies

GACCGCGTGACCATCACAGCCGATAAGTCTACCTCCACA
GCTTACATGGAGCTGTCTTCCCTGAGATCCGAGGACACC
GCCGTGTACTATTGTGCTAGGCTGGGCCGGTACTATTTC
GATTATTGGGGCCAGGGCACCACAGTGACAGTGAGCTCT
GCCAGCACAAAGGGCCCTTCCGTGTTCCCACTGGCTCCC
TGCTCCAGAAGCACATCTGAGTCCACCGCCGCTCTGGGC
TGTCTGGTGAAGGACTACTTCCCTGAGCCAGTGACCGTG
TCCTGGAACAGCGGCGCCCTGACATCTGGCGTGCACACC
TTTCCAGCTGTGCTGCAGTCCAGCGGCCTGTACTCCCTG
TCTTCCGTGGTGACAGTGCCCAGCTCTTCCCTGGGCACC
AAGACATATACCTGCAACGTGGACCATAAGCCTTCCAAT
ACCAAGGTGGATAAGAGGGTGGAGAGCAAGTACGGACCA
CCTTGCCCACCATGTCCAGCTCCTGAGTTTGAGGGAGGA
CCATCCGTGTTCCTGTTTCCTCCAAAGCCTAAGGACACC
CTGATGATCAGCCGGACACCTGAGGTGACCTGCGTGGTG
GTGGACGTGTCTCAGGAGGATCCAGAGGTGCAGTTCAAC
TGGTACGTGGATGGCGTGGAGGTGCACAATGCTAAGACC
AAGCCAAGAGAGGAGCAGTTTAATTCCACATACCGCGTG
GTGAGCGTGCTGACCGTGCTGCATCAGGATTGGCTGAAC
GGCAAGGAGTATAAGTGCAAGGTGTCCAATAAGGGCCTG
CCCAGCTCTATCGAGAAGACAATCAGCAAGGCTAAGGGA
CAGCCTAGGGAGCCACAGGTGTACACCCTGCCCCCTTCT
CAGGAGGAGATGACAAAGAACCAGGTGTCCCTGACCTGT
CTGGTGAAGGGCTTCTATCCAAGCGACATCGCTGTGGAG
TGGGAGTCTAATGGCCAGCCCGAGAACAATTACAAGACC
ACACCACCCGTGCTGGACTCTGATGGCTCCTTCTTTCTG
TATTCTAGGCTGACAGTGGATAAGTCCCGGTGGCAGGAG
GGCAACGTGTTTAGCTGCTCTGTGATGCACGAGGCCCTG
CACAATCATTATACCCAGAAGTCCCTGAGCCTGTCTCTG
GGCAAG

| | | |
|---|---|---|
| Amino acid<br>sequence of a<br>heavy chain of<br>anti-CD47<br>antibody (H0) | EVQLVQSGAEVKKPGSSVKVSCKASGYSFTHHWIHWVRQ<br>APGQGLEWMGMIDASDSETRLSQKFKDRVTITADKSTST<br>AYMELSSLRSEDTAVYYCARLGRYYFDYWGQGTTVTVSS<br>ASTKGPSVFPLAPCSRSTSESTAALGCLVKDYFPEPVTV<br>SWNSGALTSGVHTFPAVLQSSGLYSLSSVVTVPSSSLGT<br>KTYTCNVDHKPSNTKVDKRVESKYGPPCPPCPAPEFEGG<br>PSVFLFPPKPKDTLMISRTPEVTCVVVDVSQEDPEVQFN<br>WYVDGVEVHNAKTKPREEQFNSTYRVVSVLTVLHQDWLN<br>GKEYKCKVSNKGLPSSIEKTISKAKGQPREPQVYTLPPS<br>QEEMTKNQVSLTCLVKGFYPSDIAVEWESNGQPENNYKT<br>TPPVLDSDGSFFLYSRLTVDKSRWQEGNVFSCSVMHEAL<br>HNHYTQKSLSLSLGK | 4 |
| DNA<br>sequence of a<br>light chain of<br>anti-CD47<br>antibody | GAGATCGTGCTGACCCAGTCTCCAGCCACACTGTCTCTG<br>TCCCCAGGAGAGAGGGCCACCCTGAGCTGCCGGGCTTCT<br>GAGAACGTGGGCACATACATCTCCTGGTATCAGCAGAAG<br>CCAGGACAGGCTCCTAGGCTGCTGATCTACGGCGCTAGC<br>AATAGATATACCGGCATCCCTGCTCGCTTCAGCGGATCT<br>GGATCCGGCACAGACTTTACCCTGACAATCTCCAGCCTG<br>GAGCCAGAGGATTTCGCCGTGTACTATTGTGGCGAGTCC<br>TACGGCCACCTGTATACCTTTGGCGGCGGCACAAAGGTG<br>GAGATCAAGCGAACGGTGGCTGCACCATCTGTCTTCATC<br>TTCCCGCCATCTGATGAGCAGTTGAAATCTGGAACTGCC<br>TCTGTTGTGTGCCTGCTGAATAACTTCTATCCCAGAGAG<br>GCCAAAGTACAGTGGAAGGTGGATAACGCCCTCCAATCG<br>GGTAACTCCCAGGAGAGTGTCACAGAGCAGGACAGCAAG<br>GACAGCACCTACAGCCTCAGCAGCACCCTGACGCTGAGC<br>AAAGCAGACTACGAGAAACACAAAGTCTACGCCTGCGAA<br>GTCACCCATCAGGGCCTGAGCTCGCCCGTCACAAAGAGC<br>TTCAACAGGGGAGAGTGT | 5 |
| Amino acid<br>sequence of a<br>light chain of<br>anti-CD47<br>antibody (L0) | EIVLTQSPATLSLSPGERATLSCRASENVGTYISWYQQK<br>PGQAPRLLIYGASNRYTGIPARFSGSGSGTDFTLTISSL<br>EPEDFAVYYCGESYGHLYTFGGGTKVEIKRTVAAPSVFI<br>FPPSDEQLKSGTASVVCLLNNFYPREAKVQWKVDNALQS<br>GNSQESVTEQDSKDSTYSLSSTLTLSKADYEKHKVYACE<br>VTHQGLSSPVTKSFNRGEC | 6 |

TABLE 1-continued

DNA and amino acid sequences of anti-CD47
monoclonal antibodies

|  | Sequence | SEQ ID NO: | Sequence | SEQ ID NO: | Sequence | SEQ ID NO: |
|---|---|---|---|---|---|---|
| CDR sequence of a heavy chain of anti-CD47 antibody | GYSFTHHW IH | 31 | MIDASDSET RLSQKFKD | 32 | LGRYYFDY | 33 |
| CDR sequence of a light chain of anti-CD47 antibody | RASENVGT YTS | 34 | GASNRYT | 35 | GESYGHLYT | 36 |

TABLE 2

DNA and amino acid sequences of TIGIT
single domain antibodies

|  | Sequence | SEQ ID NO: |
|---|---|---|
| DNA sequence of a TIGIT single domain antibody | GAGGTGCAGCTGGTGGAGTCTGGAGGAGGACTGGTGCAG CCAGGAGGCAGCCTGAGGCTGTCTTGCGCCGCTTCCGGC TACAAGTATGGCGTGTACTCCATGGGATGGTTCAGGCAG GCTCCTGGCAAGGGACTGGAGGGCGTGTCCGCCATCTGT TCTGGCGGCAGAACCACATACTCTGACTCCGTGAAGGGC AGGTTTACCATCTCCCGGGATAACAGCAACCAGATCCTG TATCTGCAGATGAACTCCCTGAGAGCCGAGGACACCGCC GTGTACTATTGCGCTGCTAGGCCACTGTGGACAGGCGAC TGTGATCTGTCCAGCTCTTGGTATAAGACCTGGGGCCAG GGCACCCTGGTGACAGTGTCCAGC | 37 |
| Amino acid sequence of a TIGIT single domain antibody | EVQLVESGGGLVQPGGSLRLSCAASGYKYGVYSMGWFRQ APGKGLEGVSAICSGGRTTYSDSVKGRFTISRDNSNQIL YLQMNSLRAEDTAVYYCAARPLWTGDCDLSSSWYKTWGQ GTLVTVSS | 38 |

|  | Sequence | SEQ ID NO: | Sequence | SEQ ID NO: | Sequence | SEQ ID NO: |
|---|---|---|---|---|---|---|
| Amino acid sequence of CDR of a TIGIT single domain antibody | GYKYGVYS MG | 39 | AICSGGRTT YSDSVKG | 40 | RPLWTGDCDL SSSWYKT | 41 |

After being transfected with the expression plasmid, the CHO-3E7 host cells were cultured in an incubator at 37° C. and 100 rpm for 6 days. The supernatant was extracted by centrifugation, and the protein A column was used to purify the bispecific antibody protein.

As mentioned above, the CD47 monoclonal antibody was composed of a heavy chain H0 and a light chain L0. The TIGIT single domain antibody was connected to the N-terminus or C-terminus of the heavy or light chain of the CD47 monoclonal antibody through two linker sequences (E-linker: EPKSSDKTHTSPPSP (SEQ ID NO: 26) or G9-linker: GGGGSGGGS (SEQ ID NO: 28)) to generate a series of different bispecific antibodies. Firstly, the E-linker linker sequence was used to construct the following fusion proteins: (1) a new polypeptide, called H1, produced by fusing the TIGIT single domain antibody with the C-terminus of the heavy chain H0; (2) a new polypeptide H2 produced by fusing the TIGIT single domain antibody with the N-terminus of the heavy chain H0; (3) a new polypeptide L1 produced by fusing the TIGIT single domain antibody with the C-terminus of the light chain L0; and (4) a new polypeptide L2 produced by fusing the TIGIT single domain antibody with the N-terminus of the light chain L0. Similarly, the G9-linker linker sequence was then used to construct the following fusion proteins: (1) a new polypeptide, called H3, produced by fusing the TIGIT single domain antibody with the C-terminus of the heavy chain H0; (2) a new polypeptide H4 produced by fusing the TIGIT single domain antibody with the N-terminus of the heavy chain H0; (3) a new polypeptide L3 produced by fusing the TIGIT single domain antibody with the C-terminus of the light chain L0; and (4) a new polypeptide L4 produced by fusing the TIGIT single domain antibody with the N-terminus of the light chain L0.

A series of bispecific antibodies were produced by combining these constructed heavy chain fusion proteins H1, H2, H3, and H4 with the unmodified parental light chain polypeptide chain L0, or combining these constructed light chain fusion proteins L1, L2, L3, and L4 with the unmodified heavy chain polypeptide chain H0. A bispecific antibody TIGIT-E-HC was produced by combining heavy chain fusion protein H1 with parental light chain L0, a bispecific antibody TIGIT-E-HN was produced by combining heavy chain fusion protein H2 with parental light chain L0, a bispecific antibody TIGIT-G9-HC was produced by combining heavy chain fusion protein H3 with parental light chain L0, a bispecific antibody TIGIT-G9-HN was produced by combining heavy chain fusion protein H4 with parental light chain L0, a bispecific antibody TIGIT-E-LC was produced by combining light chain fusion protein L1 with parental heavy chain H0, a bispecific antibody TIGIT-E-LN was produced by combining light chain fusion protein L2 with parental heavy chain H0, a bispecific antibody TIGIT-G9-LC was produced by combining light chain fusion protein L3 with parental heavy chain H0, and a bispecific antibody TIGIT-G9-LN was produced by combining the light chain fusion protein L4 with the parental heavy chain H0. The Fc of human IgG4 was modified by site mutation (S228P and L235E), and then the TIGIT single domain antibody was connected to the N-terminus of the Fe portion of human IgG4 to produce a new fusion protein H5, thereby constructing Fc fusion protein of sdAb-TJGJT-JgG4PE.

-continued

```
TCCACTGGGTGAGGCAGGCTCCTGGACAGGGACTGGAGTGGATGGGCATG

ATCGACGCTTCCGATAGCGAGACAAGACTGTCTCAGAAGTTTAAGGACCG

CGTGACCATCACAGCCGATAAGTCTACCTCCACAGCTTACATGGAGCTGT

CTTCCCTGAGATCCGAGGACACCGCCGTGTACTATTGTGCTAGGCTGGGC

CGGTACTATTTCGATTATTGGGGCCAGGGCACCACAGTGACAGTGAGCTC

TGCCAGCACAAAGGGCCCTTCCGTGTTCCCACTGGCTCCCTGCTCCAGAA

GCACATCTGAGTCCACCGCCGCTCTGGGCTGTCTGGTGAAGGACTACTTC

CCTGAGCCAGTGACCGTGTCCTGGAACAGCGGCGCCCTGACATCTGGCGT

GCACACCTTTCCAGCTGTGCTGCAGTCCAGCGGCCTGTACTCCCTGTCTT

CCGTGGTGACAGTGCCCAGCTCTTCCCTGGGCACCAAGACATATACCTGC

AACGTGGACCATAAGCCTTCCAATACCAAGGTGGATAAGAGGGTGGAGAG

CAAGTACGGACCACCTTGCCCACCATGTCCAGCTCCTGAGTTTGAGGGAG

GACCATCCGTGTTCCTGTTTCCTCCAAAGCCTAAGGACACCCTGATGATC

AGCCGGACACCTGAGGTGACCTGCGTGGTGGTGGACGTGTCTCAGGAGGA

TCCAGAGGTGCAGTTCAACTGGTACGTGGATGGCGTGGAGGTGCACAATG
```

TABLE 3

Plasmids and proteins for construction of bispecific antibodies

| Protein | Component | Plasmid | Amino acid sequence SEQ ID NO: |
|---------|-----------|---------|--------------------------------|
| CD47 | H0 | pTT5-CD47HC | 4 |
| | L0 | pTT5-CD47LC | 6 |
| TIGIT-E-HC | H1 | pTT5-CD47HC-E-TIGIT | 8 |
| | L0 | pTT5-CD47LC | 6 |
| TIGIT-E-HN | H2 | pTT5-TIGIT-E-CD47HC | 10 |
| | L0 | pTT5-CD47LC | 6 |
| TIGIT-E-LC | L1 | pTT5-CD47LC-E-TIGIT | 16 |
| | H0 | pTT5-CD47HC | 4 |
| TIGIT-E-LN | L2 | pTT5-TIGIT-E-CD47LC | 18 |
| | H0 | pTT5-CD47HC | 4 |
| TIGIT-G9-HC | H3 | pTT5-CD47HC-G9-TIGIT | 12 |
| | L0 | pTT5-CD47LC | 6 |
| TIGIT-G9-HN | H4 | pTT5-TIGIT-G9-CD47HC | 14 |
| | L0 | pTT5-CD47LC | 6 |
| TIGIT-G9-LC | L3 | pTT5-CD47LC-G9-TIGIT | 20 |
| | H0 | pTT5-CD47HC | 4 |
| TIGIT-G9-LN | L4 | pTT5-TIGIT-G9-CD47LC | 22 |
| | H0 | pTT5-CD47HC | 4 |
| sdAb-TIGIT-IgG4PE | H5 | pTT5-sdAb-TIGIT-IgG4PE | 24 |

```
DNA sequence of secretion signal peptide
                                     (SEQ ID NO: 1)
ATGGGCTGGTCCTGCATCATCCTGTTCCTGGTGGCTACCGCCACCGGCGT

GCACTCC

Amino acid sequence of secretion signal
peptide
                                     (SEQ ID NO: 2)
MGWSCIILFLVATATGVHS DNA sequence of polypeptide chain H1
                                     (SEQ ID NO: 7)
GAGGTGCAGCTGGTGCAGTCCGGAGCTGAGGTGAAGAAGCCAGGATCCAG

CGTGAAGGTGAGCTGCAAGGCTAGCGGCTACTCTTTCACCCACCATTGGA
```

-continued

```
CTAAGACCAAGCCAAGAGAGGAGCAGTTTAATTCCACATACCGCGTGGTG

AGCGTGCTGACCGTGCTGCATCAGGATTGGCTGAACGGCAAGGAGTATAA

GTGCAAGGTGTCCAATAAGGGCCTGCCCAGCTCTATCGAGAAGACAATCA

GCAAGGCTAAGGGACAGCCTAGGGAGCCACAGGTGTACACCCTGCCCCCT

TCTCAGGAGGAGATGACAAAGAACCAGGTGTCCCTGACCTGTCTGGTGAA

GGGCTTCTATCCAAGCGACATCGCTGTGGAGTGGGAGTCTAATGGCCAGC

CCGAGAACAATTACAAGACCACACCACCCGTGCTGGACTCTGATGGCTCC

TTCTTTCTGTATTCTAGGCTGACAGTGGATAAGTCCCGGTGGCAGGAGGG

CAACGTGTTTAGCTGCTCTGTGATGCACGAGGCCCTGCACAATCATTATA
```

-continued

CCCAGAAGTCCCTGAGCCTGTCTCTGGGCAAGGAACCTAAGTCTAGCGAC

AAAACTCATACCAGCCCCCCTAGTCCAGAGGTGCAGCTGGTGGAGTCTGG

AGGAGGACTGGTGCAGCCAGGAGGCAGCCTGAGGCTGTCTTGCGCCGCTT

CCGGCTACAAGTATGGCGTGTACTCCATGGGATGGTTCAGGCAGGCTCCT

GGCAAGGGACTGGAGGGCGTGTCCGCCATCTGTTCTGGCGGCAGAACCAC

ATACTCTGACTCCGTGAAGGGCAGGTTTACCATCTCCCGGGATAACAGCA

ACCAGATCCTGTATCTGCAGATGAACTCCCTGAGAGCCGAGGACACCGCC

GTGTACTATTGCGCTGCTAGGCCACTGTGGACAGGCGACTGTGATCGTC

CAGCTCTTGGTATAAGACCTGGGGCCAGGGCACCCTGGTGACAGTGTCCA

GC

Amino acid sequence of polypeptide chain H1

(SEQ ID NO: 8)

EVQLVQSGAEVKKPGSSVKVSCKASGYSFTHHWIHWVRQAPGQGLEWMGM

IDASDSETRLSQKFKDRVTITADKSTSTAYMELSSLRSEDTAVYYCARLG

RYYFDYWGQGTTVTVSSASTKGPSVFPLAPCSRSTSESTAALGCLVKDYF

PEPVTVSWNSGALTSGVHTFPAVLQSSGLYSLSSVVTVPSSSLGTKTYTC

NVDHKPSNTKVDKRVESKYGPPCPPCPAPEFEGGPSVFLFPPKPKDTLMI

SRTPEVTCVVVDVSQEDPEVQFNWYVDGVEVHNAKTKPREEQFNSTYRVV

SVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGS

FFLYSRLTVDKSRWQEGNVFSCSVMHEALHNHYTQKSLSLSLGKEPKSSD

KTHTSPPSPEVQLVESGGGLVQPGGSLRLSCAASGYKYGVYSMGWFRQAP

GKGLEGVSAICSGGRTTYSDSVKGRFTISRDNSNQILYLQMNSLRAEDTA

VYYCAARPLWTGDCDLSSSWYKTWGQGTLVTVSS

DNA sequence of polypeptide chain H2

(SEQ ID NO: 9)

GAGGTGCAGCTGGTGGAGTCTGGAGGAGGACTGGTGCAGCCAGGAGGCAG

CCTGAGGCTGTCTTGCGCCGCTTCCGGCTACAAGTATGGCGTGTACTCCA

TGGGATGGTTCAGGCAGGCTCCTGGCAAGGGACTGGAGGGCGTGTCCGCC

ATCTGTTCTGGCGGCAGAACCACATACTCTGACTCCGTGAAGGGCAGGTT

TACCATCTCCCGGGATAACAGCAACCAGATCCTGTATCTGCAGATGAACT

CCCTGAGAGCCGAGGACACCGCCGTGTACTATTGCGCTGCTAGGCCACTG

TGGACAGGCGACTGTGATCGTCCAGCTCTTGGTATAAGACCTGGGGCCA

GGGCACCCTGGTGACAGTGTCCAGCGAACCTAAGTCTAGCGACAAAACTC

ATACCAGCCCCCCTAGTCCAGAGGTGCAGCTGGTGCAGTCCGGAGCTGAG

GTGAAGAAGCCAGGATCCAGCGTGAAGGTGAGCTGCAAGGCTAGCGGCTA

CTCTTTCACCCACCATTGGATCCACTGGGTGAGGCAGGCTCCTGGCAGG

GACTGGAGTGGATGGGCATGATCGACGCTTCCGATAGCGAGACAAGACTG

TCTCAGAAGTTTAAGGACCGCGTGACCATCACAGCCGATAAGTCTACCTC

CACAGCTTACATGGAGCTGTCTTTCCTGAGATCCGAGGACACCGCCGTGT

ACTATTGTGCTAGGCTGGGCCGGTACTATTTCGATTATTGGGGCCAGGGC

ACCACAGTGACAGTGAGCTCTGCCAGCACAAAGGGCCCTTCCGTGTTCCC

-continued

ACTGGCTCCCTGCTCCAGAAGCACATCTGAGTCCACCGCCGCTCTGGGCT

GTCTGGTGAAGGACTACTTCCCTGAGCCAGTGACCGTGTCCTGGAACAGC

GGCGCCCTGACATCTGGCGTGCACACCTTTCCAGCTGTGCTGCAGTCCAG

CGGCCTGTACTCCCTGTCTTCCGTGGTGACAGTGCCCAGCTCTTCCCTGG

GCACCAAGACATATACCTGCAACGTGGACCATAAGCCTTCCAATACCAAG

GTGGATAAGAGGGTGGAGAGCAAGTACGGACCACCTTGCCCACCATGTCC

AGCTCCTGAGTTTGAGGGAGGACCATCCGTGTTCCTGTTTCCTCCAAAGC

CTAAGGACACCCTGATGATCAGCCGGACACCTGAGGTGACCTGCGTGGTG

GTGGACGTGTCTCAGGAGGATCCAGAGGTGCAGTTCAACTGGTACGTGGA

TGGCGTGGAGGTGCACAATGCTAAGACCAAGCCAAGAGAGGAGCAGTTTA

ATTCCACATACCGCGTGGTGAGCGTGCTGACCGTGCTGCATCAGGATTGG

CTGAACGGCAAGGAGTATAAGTGCAAGGTGTCCAATAAGGGCCTGCCCAG

CTCTATCGAGAAGACAATCAGCAAGGCTAAGGGACAGCCTAGGGAGCCAC

AGGTGTACACCCTGCCCCCTTCTCAGGAGGAGATGACAAAGAACCAGGTG

TCCCTGACCTGTCTGGTGAAGGGCTTCTATCCAAGCGACATCGCTGTGGA

GTGGGAGTCTAATGGCCAGCCCGAGAACAATTACAAGACCACACCACCCG

TGCTGGACTCTGATGGCTCCTTCTTTCTGTATTCTAGGCTGACAGTGGAT

AAGTCCCGGTGGCAGGAGGGCAACGTGTTTAGCTGCTCTGTGATGCACGA

GGCCCTGCACAATCATTATACCCAGAAGTCCCTGAGCCTGTCTCTGGGCA

AG

Amino acid sequence of polypeptide chain H2

(SEQ ID NO: 10)

EVQLVESGGGLVQPGGSLRLSCAASGYKYGVYSMGWFRQAPGKGLEGVSA

ICSGGRTTYSDSVKGRFTISRDNSNQILYLQMNSLRAEDTAVYYCAARPL

WTGDCDLSSSWYKTWGQGTLVTVSSEPKSSDKTHTSPPSPEVQLVQSGAE

VKKPGSSVKVSCKASGYSFTHHWIHWVRQAPGQGLEWMGMIDASDSETRL

SQKFKDRVTITADKSTSTAYMELSSLRSEDTAVYYCARLGRYYFDYWGQG

TTVTVSSASTKGPSVFPLAPCSRSTSESTAALGCLVKDYFPEPVTVSWNS

GALTSGVHTFPAVLQSSGLYSLSSVVTVPSSSLGTKTYTCNVDHKPSNTK

VDKRVESKYGPPCPPCPAPEFEGGPSVFLFPPKPKDTLMISRTPEVTCVV

VDVSQEDPEVQFNWYVDGVEVHNAKTKPREEQFNSTYRVVSVLTVLHQDW

LNGKEYKCKVSNKGLPSSIEKTISKAKGQPREPQVYTLPPSQEEMTKNQV

SLTCLVKGFYPSDIAVEWESNGQPENNYKTTPPVLDSDGSFFLYSRLTVD

KSRWQEGNVFSCSVMHEALHNHYTQKSLSLSLGK

DNA sequence of polypeptide chain H3

(SEQ ID NO: 11)

GAGGTGCAGCTGGTGCAGTCCGGAGCTGAGGTGAAGAAGCCAGGATCCAG

CGTGAAGGTGAGCTGCAAGGCTAGCGGCTACTCTTTCACCCACCATTGGA

TCCACTGGGTGAGGCAGGCTCCTGGACAGGGACTGGAGTGGATGGGCATG

ATCGACGCTTCCGATAGCGAGACAAGACTGTCTCAGAAGTTTAAGGACCG

CGTGACCATCACAGCCGATAAGTCTACCTCCACAGCTTACATGGAGCTGT

CTTCCCTGAGATCCGAGGACACCGCCGTGTACTATTGTGCTAGGCTGGGC

CGGTACTATTTCGATTATTGGGGCCAGGGCACCACAGTGACAGTGAGCTC

-continued

TGCCAGCACAAAGGGCCCTTCCGTGTTCCCACTGGCTCCCTGCTCCAGAA

GCACATCTGAGTCCACCGCCGCTCTGGGCTGTCTGGTGAAGGACTACTTC

CCTGAGCCAGTGACCGTGTCCTGGAACAGCGGCGCCCTGACATCTGGCGT

GCACACCTTTCCAGCTGTGCTGCAGTCCAGCGGCCTGTACTCCCTGTCTT

CCGTGGTGACAGTGCCCAGCTCTTCCCTGGGCACCAAGACATATACCTGC

AACGTGGACCATAAGCCTTCCAATACCAAGGTGGATAAGAGGGTGGAGAG

CAAGTACGGACCACCTTGCCCACCATGTCCAGCTCCTGAGTTTGAGGGAG

GACCATCCGTGTTCCTGTTTCCTCCAAAGCCTAAGGACACCCTGATGATC

AGCCGGACACCTGAGGTGACCTGCGTGGTGGTGGACGTGTCTCAGGAGGA

TCCAGAGGTGCAGTTCAACTGGTACGTGGATGGCGTGGAGGTGCACAATG

CTAAGACCAAGCCAAGAGAGGAGCAGTTTAATTCCACATACCGCGTGGTG

AGCGTGCTGACCGTGCTGCATCAGGATTGGCTGAACGGCAAGGAGTATAA

GTGCAAGGTGTCCAATAAGGGCCTGCCCAGCTCTATCGAGAAGACAATCA

GCAAGGCTAAGGGACAGCCTAGGGAGCCACAGGTGTACACCCTGCCCCCT

TCTCAGGAGGAGATGACAAAGAACCAGGTGTCCCTGACCTGTCTGGTGAA

GGGCTTCTATCCAAGCGACATCGCTGTGGAGTGGGAGTCTAATGGCCAGC

CCGAGAACAATTACAAGACCACACCACCCGTGCTGGACTCTGATGGCTCC

TTCTTTCTGTATTCTAGGCTGACAGTGGATAAGTCCCGGTGGCAGGAGGG

CAACGTGTTTAGCTGCTCTGTGATGCACGAGGCCCTGCACAATCATTATA

CCCAGAAGTCCCTGAGCCTGTCTCTGGGCAAGGGTGGAGGCGGTAGTGGA

GGCGGTTCAGAGGTGCAGCTGGTGGAGTCTGGAGGAGGACTGGTGCAGCC

AGGAGGCAGCCTGAGGCTGTCTTGCGCCGCTTCCGGCTACAAGTATGGCG

TGTACTCCATGGGATGGTTCAGGCAGGCTCCTGGCAAGGGACTGGAGGGC

GTGTCCGCCATCTGTTCTGGCGGCAGAACCACATACTCTGACTCCGTGAA

GGGCAGGTTTACCATCTCCCGGGATAACAGCAACCAGATCCTGTATCTGC

AGATGAACTCCCTGAGAGCCGAGGACACCGCCGTGTACTATTGCGCTGCT

AGGCCACTGTGGACAGGCGACTGTGATCTGTCCAGCTCTTGGTATAAGAC

CTGGGGCCAGGGCACCCTGGTGACAGTGTCCAGC

Amino acid sequence of polypeptide chain H3
(SEQ ID NO: 12)

EVQLVQSGAEVKKPGSSVKVSCKASGYSFTHHWIHWVRQAPGQGLEWMGM

IDASDSETRLSQKFKDRVTITADKSTSTAYMELSSLRSEDTAVYYCARLG

RYYFDYWGQGTTVTVSSASTKGPSVFPLAPCSRSTSESTAALGCLVKDYF

PEPVTVSWNSGALTSGVHTFPAVLQSSGLYSLSSVVTVPSSSLGTKTYTC

NVDHKPSNTKVDKRVESKYGPPCPPCPAPEFEGGPSVFLFPPKPKDTLMI

SRTPEVTCVVVDVSQEDPEVQFNWYVDGVEVHNAKTKPREEQFNSTYRVV

SVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGS

FFLYSRLTVDKSRWQEGNVFSCSVMHEALHNHYTQKSLSLSLGKGGGGSG

GGSEVQLVESGGGLVQPGGSLRLSCAASGYKYGVYSMGWFRQAPGKGLEG

-continued

VSAICSGGRTTYSDSVKGRFTISRDNSNQILYLQMNSLRAEDTAVYYCAA

RPLWTGDCDLSSSWYKTWGQGTLVTVSS

DNA sequence of polypeptide chain H4

(SEQ ID NO: 13)

GAGGTGCAGCTGGTGGAGTCTGGAGGAGGACTGGTGCAGCCAGGAGGCAG

CCTGAGGCTGTCTTGCGCCGCTTCCGGCTACAAGTATGGCGTGTACTCCA

TGGGATGGTTCAGGCAGGCTCCTGGCAAGGGACTGGAGGGCGTGTCCGCC

ATCTGTTCTGGCGGCAGAACCACATACTCTGACTCCGTGAAGGGCAGGTT

TACCATCTCCCGGGATAACAGCAACCAGATCCTGTATCTGCAGATGAACT

CCCTGAGAGCCGAGGACACCGCCGTGTACTATTGCGCTGCTAGGCCACTG

TGGACAGGCGACTGTGATCTGTCCAGCTCTTGGTATAAGACCTGGGGCCA

GGGCACCCTGGTGACAGTGTCCAGCGGTGGAGGCGGTAGTGGAGGCGGTT

CAGAGGTGCAGCTGGTGCAGTCCGGAGCTGAGGTGAAGAAGCCAGGATCC

AGCGTGAAGGTGAGCTGCAAGGCTAGCGGCTACTCTTTCACCCACCATTG

GATCCACTGGGTGAGGCAGGCTCCTGGACAGGGACTGGAGTGGATGGGCA

TGATCGACGCTTCCGATAGCGAGACAAGACTGTCTCAGAAGTTTAAGGAC

CGCGTGACCATCACAGCCGATAAGTCTACCTCCACAGCTTACATGGAGCT

GTCTTCCCTGAGATCCGAGGACACCGCCGTGTACTATTGTGCTAGGCTGG

GCCGGTACTATTTCGATTATTGGGGCCAGGGCACCACAGTGACAGTGAGC

TCTGCCAGCACAAAGGGCCCTTCCGTGTTCCCACTGGCTCCCTGCTCCAG

AAGCACATCTGAGTCCACCGCCGCTCTGGGCTGTCTGGTGAAGGACTACT

TCCCTGAGCCAGTGACCGTGTCCTGGAACAGCGGCGCCCTGACATCTGGC

GTGCACACCTTTCCAGCTGTGCTGCAGTCCAGCGGCCTGTACTCCCTGTC

TTCCGTGGTGACAGTGCCCAGCTCTTCCCTGGGCACCAAGACATATACCT

GCAACGTGGACCATAAGCCTTCCAATACCAAGGTGGATAAGAGGGTGGAG

AGCAAGTACGGACCACCTTGCCCACCATGTCCAGCTCCTGAGTTTGAGGG

AGGACCATCCGTGTTCCTGTTTCCTCCAAAGCCTAAGGACACCCTGATGA

TCAGCCGGACACCTGAGGTGACCTGCGTGGTGGTGGACGTGTCTCAGGAG

GATCCAGAGGTGCAGTTCAACTGGTACGTGGATGGCGTGGAGGTGCACAA

TGCTAAGACCAAGCCAAGAGAGGAGCAGTTTAATTCCACATACCGCGTGG

TGAGCGTGCTGACCGTGCTGCATCAGGATTGGCTGAACGGCAAGGAGTAT

AAGTGCAAGGTGTCCAATAAGGGCCTGCCCAGCTCTATCGAGAAGACAAT

CAGCAAGGCTAAGGGACAGCCTAGGGAGCCACAGGTGTACACCCTGCCCC

CTTCTCAGGAGGAGATGACAAAGAACCAGGTGTCCCTGACCTGTCTGGTG

AAGGGCTTCTATCCAAGCGACATCGCTGTGGAGTGGGAGTCTAATGGCCA

GCCCGAGAACAATTACAAGACCACACCACCCGTGCTGGACTCTGATGGCT

CCTTCTTTCTGTATTCTAGGCTGACAGTGGATAAGTCCCGGTGGCAGGAG

GGCAACGTGTTTAGCTGCTCTGTGATGCACGAGGCCCTGCACAATCATTA

TACCCAGAAGTCCCTGAGCCTGTCTCTGGGCAAG

-continued

Amino acid sequence of polypeptide chain H4

(SEQ ID NO: 14)

EVQLVESGGGLVQPGGSLRLSCAASGYKYGVYSMGWFRQAPGKGLEGVSA

ICSGGRTTYSDSVKGRFTISRDNSNQILYLQMNSLRAEDTAVYYCAARPL

WTGDCDLSSSWYKTWGQGTLVTVSSGGGGSGGGSEVQLVQSGAEVKKPGS

SVKVSCKASGYSFTHHWIHWVRQAPGQGLEWMGMIDASDSETRLSQKFKD

RVTITADKSTSTAYMELSSLRSEDTAVYYCARLGRYYFDYWGQGTTVTVS

SASTKGPSVFPLAPCSRSTSESTAALGCLVKDYFPEPVTVSWNSGALTSG

VHTFPAVLQSSGLYSLSSVVTVPSSSLGTKTYTCNVDHKPSNTKVDKRVE

SKYGPPCPPCPAPEFEGGPSVFLFPPKPKDTLMISRTPEVTCVVVDVSQE

DPEVQFNWYVDGVEVHNAKTKPREEQFNSTYRVVSVLTVLHQDWLNGKEY

KCKVSNKGLPSSIEKTISKAKGQPREPQVYTLPPSQEEMTKNQVSLTCLV

KGFYPSDIAVEWESNGQPENNYKTTPPVLDSDGSFFLYSRLTVDKSRWQE

GNVFSCSVMHEALHNHYTQKSLSLSLGK

DNA sequence of polypeptide chain L1

(SEQ ID NO: 15)

GAGATCGTGCTGACCCAGTCTCCAGCCACACTGTCTCTGTCCCCAGGAGA

GAGGGCCACCCTGAGCTGCCGGGCTTCTGAGAACGTGGGCACATACATCT

CCTGGTATCAGCAGAAGCCAGGACAGGCTCCTAGGCTGCTGATCTACGGC

GCTAGCAATAGATATACCGGCATCCCTGCTCGCTTCAGCGGATCTGGATC

CGGCACAGACTTTACCCTGACAATCTCCAGCCTGGAGCCAGAGGATTTCG

CCGTGTACTATTGTGGCGAGTCCTACGGCCACCTGTATACCTTTGGCGGC

GGCACAAAGGTGGAGATCAAGCGAACGGTGGCTGCACCATCTGTCTTCAT

CTTCCCGCCATCTGATGAGCAGTTGAAATCTGGAACTGCCTCTGTTGTGT

GCCTGCTGAATAACTTCTATCCCAGAGAGGCCAAAGTACAGTGGAAGGTG

GATAACGCCCTCCAATCGGGTAACTCCCAGGAGAGTGTCACAGAGCAGGA

CAGCAAGGACAGCACCTACAGCCTCAGCAGCACCCTGACGCTGAGCAAAG

CAGACTACGAGAAACACAAAGTCTACGCCTGCGAAGTCACCCATCAGGGC

CTGAGCTCGCCCGTCACAAAGAGCTTCAACAGGGGGAGAGTGTGAACCTAA

GTCTAGCGACAAAACTCATACCAGCCCCCCTAGTCCAGAGGTGCAGCTGG

TGGAGTCTGGAGGAGGACTGGTGCAGCCAGGAGGCAGCCTGAGGCTGTCT

TGCGCCGCTTCCGGCTACAAGTATGGCGTGTACTCCATGGGATGGTTCAG

GCAGGCTCCTGGCAAGGGACTGGAGGGCGTGTCCGCCATCTGTTCTGGCG

GCAGAACCACATACTCTGACTCCGTGAAGGGCAGGTTTACCATCTCCCGG

GATAACAGCAACCAGATCCTGTATCTGCAGATGAACTCCCTGAGAGCCGA

GGACACCGCCGTGTACTATTGCGCTGCTAGGCCACTGTGGACAGGCGACT

GTGATCGTCCAGCTCTTGGTATAAGACCTGGGGCCAGGGCACCCTGGTG

ACAGTGTCCAGC

Amino acid sequence of polypeptide chain L1

(SEQ ID NO: 16)

EIVLTQSPATLSLSPGERATLSCRASENVGTYISWYQQKPGQAPRLLIYG

ASNRYTGIPARFSGSGSGTDFTLTISSLEPEDFAVYYCGESYGHLYTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

-continued

LSSPVTKSFNRGECEPKSSDKTHTSPPSPEVQLVESGGGLVQPGGSLRLS

CAASGYKYGVYSMGWFRQAPGKGLEGVSAICSGGRTTYSDSVKGRFTISR

DNSNQILYLQMNSLRAEDTAVYYCAARPLWTGDCDLSSSWYKTWGQGTLV

TVSS

DNA sequence of polypeptide chain L2

(SEQ ID NO: 17)

GAGGTGCAGCTGGTGGAGTCTGGAGGAGGACTGGTGCAGCCAGGAGGCAG

CCTGAGGCTGTCTTGCGCCGCTTCCGGCTACAAGTATGGCGTGTACTCCA

TGGGATGGTTCAGGCAGGCTCCTGGCAAGGGACTGGAGGGCGTGTCCGCC

ATCTGTTCTGGCGGCAGAACCACATACTCTGACTCCGTGAAGGGCAGGTT

TACCATCTCCCGGGATAACAGCAACCAGATCCTGTATCTGCAGATGAACT

CCCTGAGAGCCGAGGACACCGCCGTGTACTATTGCGCTGCTAGGCCACTG

TGGACAGGCGACTGTGATCGTCCAGCTCTTGGTATAAGACCTGGGGCCA

GGGCACCCTGGTGACAGTGTCCAGCGAACCTAAGTCTAGCGACAAAACTC

ATACCAGCCCCCCTAGTCCAGAGATCGTGCTGACCCAGTCTCCAGCCACA

CTGTCTCTGTCCCCAGGAGAGAGGGCCACCCTGAGCTGCCGGGCTTCTGA

GAACGTGGGCACATACATCTCCTGGTATCAGCAGAAGCCAGGACAGGCTC

CTAGGCTGCTGATCTACGGCGCTAGCAATAGATATACCGGCATCCCTGCT

CGCTTCAGCGGATCTGGATCCGGCACAGACTTTACCCTGACAATCTCCAG

CCTGGAGCCAGAGGATTTCGCCGTGTACTATTGTGGCGAGTCCTACGGCC

ACCTGTATACCTTTGGCGGCGGCACAAAGGTGGAGATCAAGCGAACGGTG

GCTGCACCATCTGTCTTCATCTTCCCGCCATCTGATGAGCAGTTGAAATC

TGGAACTGCCTCTGTTGTGTGCCTGCTGAATAACTTCTATCCCAGAGAGG

CCAAAGTACAGTGGAAGGTGGATAACGCCCTCCAATCGGGTAACTCCCAG

GAGAGTGTCACAGAGCAGGACAGCAAGGACAGCACCTACAGCCTCAGCAG

CACCCTGACGCTGAGCAAAGCAGACTACGAGAAACACAAAGTCTACGCCT

GCGAAGTCACCCATCAGGGCCTGAGCTCGCCCGTCACAAAGAGCTTCAAC

AGGGGAGAGTGT

Amino acid sequence of polypeptide chain L2

(SEQ ID NO: 18)

EVQLVESGGGLVQPGGSLRLSCAASGYKYGVYSMGWFRQAPGKGLEGVSA

ICSGGRTTYSDSVKGRFTISRDNSNQILYLQMNSLRAEDTAVYYCAARPL

WTGDCDLSSSWYKTWGQGTLVTVSSEPKSSDKTHTSPPSPEIVLTQSPAT

LSLSPGERATLSCRASENVGTYISWYQQKPGQAPRLLIYGASNRYTGIPA

RFSGSGSGTDFTLTISSLEPEDFAVYYCGESYGHLYTFGGGTKVEIKRTV

AAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFN

RGEC

DNA sequence of polypeptide chain L3

(SEQ ID NO: 19)

GAGATCGTGCTGACCCAGTCTCCAGCCACACTGTCTCTGTCCCCAGGAGA

GAGGGCCACCCTGAGCTGCCGGGCTTCTGAGAACGTGGGCACATACATCT

CCTGGTATCAGCAGAAGCCAGGACAGGCTCCTAGGCTGCTGATCTACGGC

-continued

```
GCTAGCAATAGATATACCGGCATCCCTGCTCGCTTCAGCGGATCTGGATC

CGGCACAGACTTTACCCTGACAATCTCCAGCCTGGAGCCAGAGGATTTCG

CCGTGTACTATTGTGGCGAGTCCTACGGCCACCTGTATACCTTTGGCGGC

GGCACAAAGGTGGAGATCAAGCGAACGGTGGCTGCACCATCTGTCTTCAT

CTTCCCGCCATCTGATGAGCAGTTGAAATCTGGAACTGCCTCTGTTGTGT

GCCTGCTGAATAACTTCTATCCCAGAGAGGCCAAAGTACAGTGGAAGGTG

GATAACGCCCTCCAATCGGGTAACTCCCAGGAGAGTGTCACAGAGCAGGA

CAGCAAGGACAGCACCTACAGCCTCAGCAGCACCCTGACGCTGAGCAAAG

CAGACTACGAGAACACAAAGTCTACGCCTGCGAAGTCACCCATCAGGGC

CTGAGCTCGCCCGTCACAAAGAGCTTCAACAGGGGAGAGTGTGGTGGAGG

CGGTAGTGGAGGCGGTTCAGAGGTGCAGCTGGTGGAGTCTGGAGGAGGAC

TGGTGCAGCCAGGAGGCAGCCTGAGGCTGTCTTGCGCCGCTTCCGGCTAC

AAGTATGGCGTGTACTCCATGGGATGGTTCAGGCAGGCTCCTGGCAAGGG

ACTGGAGGGCGTGTCCGCCATCTGTTCTGGCGGCAGAACCACATACTCTG

ACTCCGTGAAGGGCAGGTTTACCATCTCCCGGGATAACAGCAACCAGATC

CTGTATCTGCAGATGAACTCCCTGAGAGCCGAGGACACCGCCGTGTACTA

TTGCGCTGCTAGGCCACTGTGGACAGGCGACTGTGATCTGTCCAGCTCTT

GGTATAAGACCTGGGGCCAGGGCACCCTGGTGACAGTGTCCAGC
```

Amino acid sequence of polypeptide chain L3
```
                                         (SEQ ID NO: 20)
EIVLTQSPATLSLSPGERATLSCRASENVGTYISWYQQKPGQAPRLLIYG

ASNRYTGIPARFSGSGSGTDFTLTISSLEPEDFAVYYCGESYGHLYTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGECGGGGSGGGGSEVQLVESGGGLVQPGGSLRLSCAASGY

KYGVYSMGWFRQAPGKGLEGVSAICSGGRTTYSDSVKGRFTISRDNSNQI

LYLQMNSLRAEDTAVYYCAARPLWTGDCDLSSSWYKTWGQGTLVTVSS
```

DNA sequence of polypeptide chain L4
```
                                         (SEQ ID NO: 21)
GAGGTGCAGCTGGTGGAGTCTGGAGGAGGACTGGTGCAGCCAGGAGGCAG

CCTGAGGCTGTCTTGCGCCGCTTCCGGCTACAAGTATGGCGTGTACTCCA

TGGGATGGTTCAGGCAGGCTCCTGGCAAGGGACTGGAGGGCGTGTCCGCC

ATCTGTTCTGGCGGCAGAACCACATACTCTGACTCCGTGAAGGGCAGGTT

TACCATCTCCCGGGATAACAGCAACCAGATCCTGTATCTGCAGATGAACT

CCCTGAGAGCCGAGGACACCGCCGTGTACTATTGCGCTGCTAGGCCACTG

TGGACAGGCGACTGTGATCTGTCCAGCTCTTGGTATAAGACCTGGGGCCA

GGGCACCCTGGTGACAGTGTCCAGCGGTGGAGGCGGTAGTGGAGGCGGTT

CAGAGATCGTGCTGACCCAGTCTCCAGCCACACTGTCTCTGTCCCCAGGA

GAGAGGGCCACCCTGAGCTGCCGGGCTTCTGAGAACGTGGGCACATACAT

CTCCTGGTATCAGCAGAAGCCAGGACAGGCTCCTAGGCTGCTGATCTACG

GCGCTAGCAATAGATATACCGGCATCCCTGCTCGCTTCAGCGGATCTGGA

TCCGGCACAGACTTTACCCTGACAATCTCCAGCCTGGAGCCAGAGGATTT

CGCCGTGTACTATTGTGGCGAGTCCTACGGCCACCTGTATACCTTTGGCG
```

-continued

```
GCGGCACAAAGGTGGAGATCAAGCGAACGGTGGCTGCACCATCTGTCTTC

ATCTTCCCGCCATCTGATGAGCAGTTGAAATCTGGAACTGCCTCTGTTGT

GTGCCTGCTGAATAACTTCTATCCCAGAGAGGCCAAAGTACAGTGGAAGG

TGGATAACGCCCTCCAATCGGGTAACTCCCAGGAGAGTGTCACAGAGCAG

GACAGCAAGGACAGCACCTACAGCCTCAGCAGCACCCTGACGCTGAGCAA

AGCAGACTACGAGAACACAAAGTCTACGCCTGCGAAGTCACCCATCAGG

GCCTGAGCTCGCCCGTCACAAAGAGCTTCAACAGGGGAGAGTGT
```

Amino acid sequence of polypeptide chain L4
```
                                         (SEQ ID NO: 22)
EVQLVESGGGLVQPGGSLRLSCAASGYKYGVYSMGWFRQAPGKGLEGVSA

ICSGGRTTYSDSVKGRFTISRDNSNQILYLQMNSLRAEDTAVYYCAARPL

WTGDCDLSSSWYKTWGQGTLVTVSSGGGGSGGGGSEIVLTQSPATLSLSPG

ERATLSCRASENVGTYISWYQQKPGQAPRLLIYGASNRYTGIPARFSGSG

SGTDFTLTISSLEPEDFAVYYCGESYGHLYTFGGGTKVEIKRTVAAPSVF

IFPPSDEQLKSGTASVVCLLNNFYPREAKVQWKVDNALQSGNSQESVTEQ

DSKDSTYSLSSTLTLSKADYEKHKVYACEVTHQGLSSPVTKSFNRGEC
```

DNA sequence of polypeptide chain H5
```
                                         (SEQ ID NO: 23)
GAGGTGCAGCTGGTGGAGTCTGGAGGAGGACTGGTGCAGCCAGGAGGCAG

CCTGAGGCTGTCTTGCGCCGCTTCCGGCTACAAGTATGGCGTGTACTCCA

TGGGATGGTTCAGGCAGGCTCCTGGCAAGGGACTGGAGGGCGTGTCCGCC

ATCTGTTCTGGCGGCAGAACCACATACTCTGACTCCGTGAAGGGCAGGTT

TACCATCTCCCGGGATAACAGCAACCAGATCCTGTATCTGCAGATGAACT

CCCTGAGAGCCGAGGACACCGCCGTGTACTATTGCGCTGCTAGGCCACTG

TGGACAGGCGACTGTGATCTGTCCAGCTCTTGGTATAAGACCTGGGGCCA

GGGCACCCTGGTGACAGTGTCCAGCGAGAGCAAGTACGGACCACCTTGCC

CACCATGTCCAGCTCCTGAGTTTGAGGGAGGACCATCCGTGTTCCTGTTT

CCTCCAAAGCCTAAGGACACCCTGATGATCAGCCGGACACCTGAGGTGAC

CTGCGTGGTGGTGGACGTGTCTCAGGAGGATCCAGAGGTGCAGTTCAACT

GGTACGTGGATGGCGTGGAGGTGCACAATGCTAAGACCAAGCCAAGAGAG

GAGCAGTTTAATTCCACATACCGCGTGGTGAGCGTGCTGACCGTGCTGCA

TCAGGATTGGCTGAACGGCAAGGAGTATAAGTGCAAGGTGTCCAATAAGG

GCCTGCCCAGCTCTATCGAGAAGACAATCAGCAAGGCTAAGGGACAGCCT

AGGGAGCCACAGGTGTACACCCTGCCCCCTTCTCAGGAGGAGATGACAAA

GAACCAGGTGTCCCTGACCTGTCTGGTGAAGGGCTTCTATCCAAGCGACA

TCGCTGTGGAGTGGGAGTCTAATGGCCAGCCCGAGAACAATTACAAGACC

ACACCACCCGTGCTGGACTCTGATGGCTCCTTCTTTCTGTATTCTAGGCT

GACAGTGGATAAGTCCCGGTGGCAGGAGGGCAACGTGTTTAGCTGCTCTG

TGATGCACGAGGCCCTGCACAATCATTATACCCAGAAGTCCCTGAGCCTG

TCTCTGGGCAAG
```

-continued

Amino acid sequence of polypeptide chain H5

(SEQ ID NO: 24)

EVQLVESGGGLVQPGGSLRLSCAASGYKYGVYSMGWFRQAPGKGLEGVSA

ICSGGRTTYSDSVKGRFTISRDNSNQILYLQMNSLRAEDTAVYYCAARPL

WTGDCDLSSSWYKTWGQGTLVTVSSESKYGPPCPPCPAPEFEGGPSVFLF

PPKPKDTLMISRTPEVTCVVVDVSQEDPEVQFNWYVDGVEVHNAKTKPRE

EQFNSTYRVVSVLTVLHQDWLNGKEYKCKVSNKGLPSSIEKTISKAKGQP

REPQVYTLPPSQEEMTKNQVSLTCLVKGFYPSDIAVEWESNGQPENNYKT

TPPVLDSDGSFFLYSRLTVDKSRWQEGNVFSCSVMHEALHNHYTQKSLSL

SLGK

DNA sequence of E-linker linker (SEQ ID NO: 25)

GAACCTAAGTCTAGCGACAAAACTCATACCAGCCCCCCTAGTCCA

Amino acid sequence of E-linker linker (SEQ ID NO: 26)

EPKSSDKTHTSPPSP

DNA sequence of G9-linker linker (SEQ ID NO: 27)

GGTGGaGGCGGTAGTGGAGGCGGTTCA

Amino acid sequence of G9-linker linker (SEQ ID NO: 28)

GGGGSGGGS

DNA sequence of IgG4 Fc (SEQ ID NO: 29)

GAGAGCAAGTACGGACCACCTTGCCCACCATGTCCAGCTCCTGAGTTTGA

GGGAGGACCATCCGTGTTCCTGTTTCCTCCAAAGCCTAAGGACACCCTGA

TGATCAGCCGGACACCTGAGGTGACCTGCGTGGTGGTGGACGTGTCTCAG

GAGGATCCAGAGGTGCAGTTCAACTGGTACGTGGATGGCGTGGAGGTGCA

CAATGCTAAGACCAAGCCAAGAGAGGAGCAGTTTAATTCCACATACCGCG

TGGTGAGCGTGCTGACCGTGCTGCATCAGGATTGGCTGAACGGCAAGGAG

TATAAGTGCAAGGTGTCCAATAAGGGCCTGCCCAGCTCTATCGAGAAGAC

AATCAGCAAGGCTAAGGGACAGCCTAGGGAGCCACAGGTGTACACCCTGC

CCCCTTCTCAGGAGGAGATGACAAAGAACCAGGTGTCCCTGACCTGTCTG

GTGAAGGGCTTCTATCCAAGCGACATCGCTGTGGAGTGGGAGTCTAATGG

CCAGCCCGAGAACAATTACAAGACCACACCACCCGTGCTGGACTCTGATG

GCTCCTTCTTTCTGTATTCTAGGCTGACAGTGGATAAGTCCCGGTGGCAG

GAGGGCAACGTGTTTAGCTGCTCTGTGATGCACGAGGCCCTGCACAATCA

TTATACCCAGAAGTCCCTGAGCCTGTCTCTGGGCAAG

Amino acid sequence of IgG4 Fc (SEQ ID NO: 30)

ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK

Example 2 Affinity Analysis by FACS

For the series of constructed bispecific antibody samples, flow cytometry was used to determine the affinity of these samples for antigen. The sample had an initial concentration of 300 nm and was diluted in a 3-fold gradient. And then, the affinity of the samples having different concentrations to the TIGIT antigen or CD47 antigen expressed on CHO-K1 cells were tested, respectively. Next, the geometric mean was used to generate an antibody-antigen binding curve, the original data of the four parameters were plotted using GRAPHPAD Prism V6.02 software, and a best-fit program was compiled to analyze the $EC_{50}$.

For the affinity analysis of TIGIT antigen, after the bispecific antibody produced by fusing the TIGIT single domain antibody to the N-terminus or C-terminus of the heavy or light chain of a CD47 monoclonal antibody (mAb) was incubated on CHO-K1 cells expressing TIGIT antigen, FACS detection showed that compared with the TIGIT single domain antibody control fused to IgG4 Fc (sdAb-TIGIT-IgG4PE), the affinity of the bispecific antibody produced by fusing the TIGIT single domain antibody to the N-terminus of the heavy or light chain of the CD47 monoclonal antibody (mAb) with TIGIT antigen was significantly higher than that of the single domain antibody control (FIG. 1). However, the affinity of the bispecific antibody produced by fusing the TIGIT single domain antibody to the C-terminus of the heavy or light chain of a CD47 monoclonal antibody (mAb) with the TIGIT antigen was lower than that of the single-domain antibody control. Therefore, when the TIGIT single domain antibody was connected to the N-terminus of the CD47 monoclonal antibody, the binding of the TIGIT single domain antibody to the TIGIT antigen would be enhanced, and when the TIGIT single domain antibody was connected to the C-terminus of the CD47 monoclonal antibody, the affinity of the TIGIT single domain antibody with the TIGIT antigen would be reduced.

Figure 2:
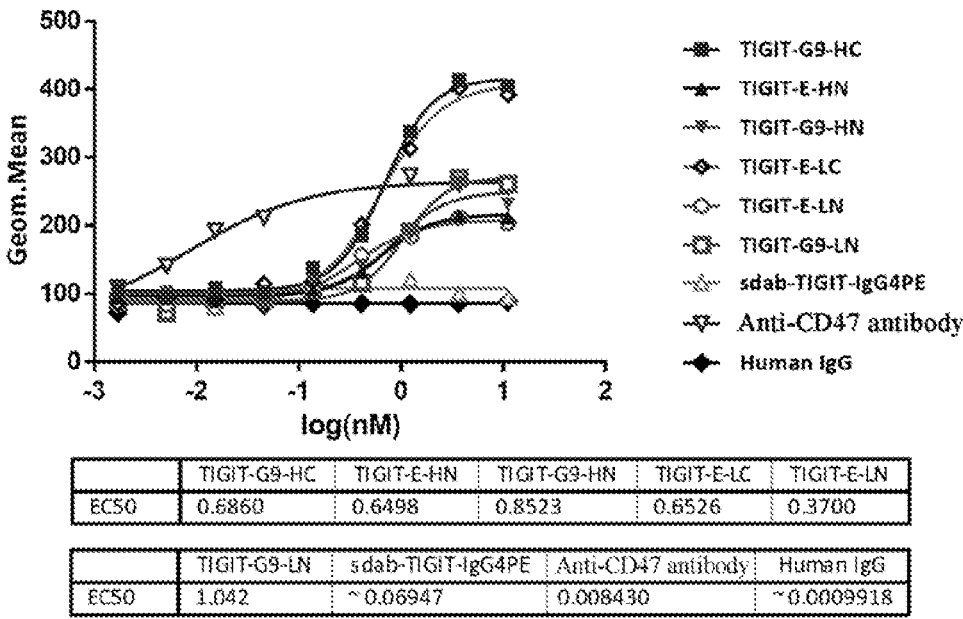

For the affinity analysis of CD47 antigen, the bispecific antibody produced by fusing TIGIT single domain antibody to the terminus of the heavy or light chain of a CD47 monoclonal antibody (mAb) was incubated on CHO-K1 cells expressing CD47 antigen, FACS detection showed that compared with the CD47 monoclonal antibody control, the $EC_{50}$ values for the binding of all the bispecific antibody samples to the CD47 antigen were higher than the $EC_{50}$ values for the binding of the CD47 monoclonal antibody to the CD47 antigen (FIG. 2). This difference in affinity implied that the TIGIT single domain antibody was connected to the CD47 monoclonal antibody, which would interfere with the binding of the CD47 monoclonal antibody to the CD47 antigen to a certain extent, thereby resulting in a decrease in the affinity of the constructed bispecific antibody with the CD47 antigen.

Example 3 Biological Activity Assay In Vitro

For the biological activity assay in vitro of the CD47/TIGIT bispecific antibody, since there was no analytical system that could detect both CD47 and TIGIT blockers at the same time, the Promega detection kit was used for the TIGIT blocker bioassay, and then the cell phagocytosis test of anti-CD47 antibody was used to determine the activity of the bispecific antibody.

Promega's TIGIT/CD155 blocking bioassay system could be used to determine the biological activity of antibodies or other biological agents that could block the TIGIT/CD155 interaction. The test consisted of two genetically engineered cell lines: TIGIT effector cells, that was, jurkat T cells expressing human TIGIT and a luciferase reporter gene driven by a natural promoter that responded to TCR activation and CD226 co-stimulation; CD155 aAPC/CHO-K1 cells were CHO-K1 cells that expressed human CD155 and a cell surface protein that could activate the TCR complex in an antigen-independent manner. When the two cell types were co-cultured, TIGIT inhibited CD226 activation and promoter-mediated luminescence. The addition of anti-TIGIT antibody could block the interaction between TIGIT and CD155 or inhibit the ability of TIGIT to prevent CD226 from forming a homodimer, thereby restoring the promoter-mediated luminescence.

When testing the activity of anti-TIGIT antibodies, the effector cell line Jurkat T cells were first plated in a 96-well plate, and then anti-TIGIT monoclonal antibody samples and the stimulatory cell line CD155 aAPC/CHO-K1 cells were added. The system was incubated at 37° C. for 6 hours. After that, Bio-Glo™ fluorescence detection reagent was added and incubated at room temperature for 5-10 minutes. Finally, a chemical fluorescence signal plate reader was used to read the fluorescence signal in the 96-well plate. In this test, 8 concentrations were used and three replicate wells were set for each concentration. A four-parameter curve was plotted with the relative fluorescence value as the y-axis and the concentration of the antibody sample as the x-axis. GraphPad Prism software was used to analyze the curve and the $EC_{50}$ value of the anti-TIGIT monoclonal antibody sample was obtained.

For the cell phagocytosis test of anti-CD47 antibody, PBMC was firstly extracted from human peripheral blood via a concentration gradient method. After that, a whole monocyte separation kit (Miltenyi Biotech) was used to separate monocytes from PBMC. These monocytes were stimulated into macrophages with GM-CSF over a period of 14 days. At day 14, HL60 cells were stained with PKH26 dye and seeded in a 96-well culture plate, MDM was digested from the culture dish with Accutase, and then MDM was added to the culture plate with HL60 stained by PKH26. In addition, a gradiently diluted anti-CD47 antibody samples were added and incubated at 37° C. for 1 hour to allow the cell phagocytosis reaction to proceed. One hour later, the MDM was digested from the cell culture dish and a fluorescently labeled anti-CD11b antibody was used to stain the MDM. After that, BD FACSCalibur flow cytometry was then used to analyze the cells in the cell plate. The percentage of phagocytosis was calculated by dividing the number of PKH26 and CD11b double positive cells by the number of PKH26 single positive cells. The dose-effect curve graph was plotted with the percentage of phagocytosis as the y-axis and the concentration of anti-CD47 antibody as the x-axis, and GraphPad Prism software was used to analyze and obtain the $EC_{50}$ value and other curve parameters.

Figure 3:
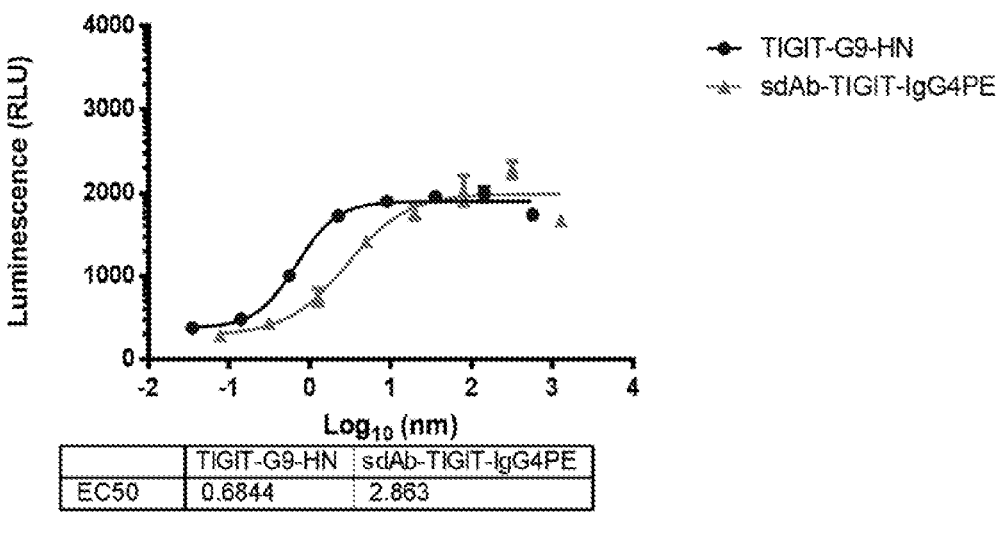

The biological activity assay results based on the TIGIT/CD155 blocker showed that the bispecific antibody TIGIT-G9-HN had a higher biological activity than the TIGIT single domain antibody control (sdAb-TIGIT-IgG4PE) (FIG. 3). The TIGIT single domain antibody in this bispecific antibody was fused to the N-terminus of the heavy chain of the CD47 monoclonal antibody (mAb), and the affinity analysis results by FACS showed that its affinity was significantly higher than that of the TIGIT single domain antibody control. The consistency of affinity and biological activity in vitro further confirmed that this bispecific antibody enhanced the activity of the TIGIT single domain antibody.

Figure 4:
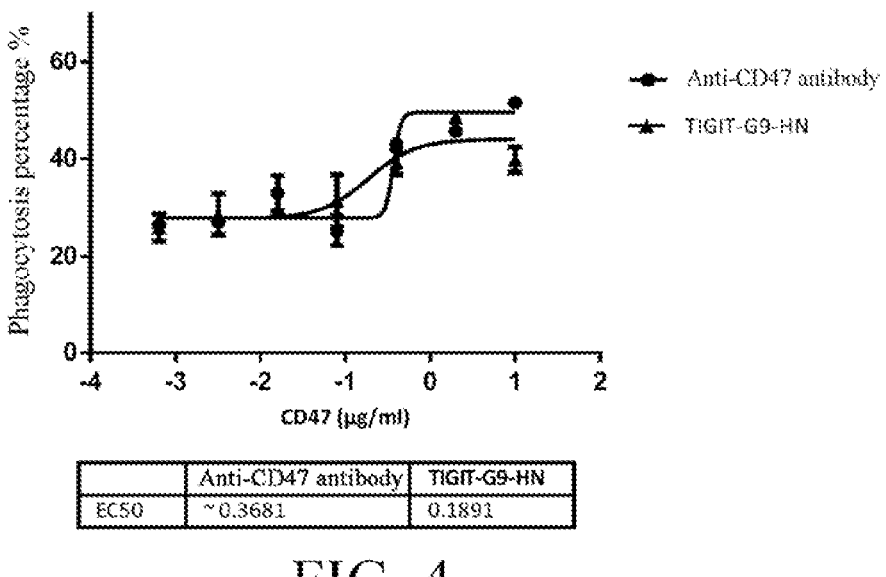

The cell phagocytosis test results of anti-CD47 antibody showed that the $EC_{50}$ value of the bispecific antibody TIGIT-G9-HN was slightly lower than that of the CD47 control antibody (FIG. 4). The affinity analysis results by FACS showed that its affinity was lower than that of the CD47 monoclonal antibody control, which indicated that the reduction of affinity had little effect on the biological activity in vitro of this bispecific antibody.

What is claimed is:

1. An isolated anti-CD47/anti-TIGIT bispecific antigen binding protein comprising (a) a first antigen binding portion comprising an anti-CD47 antibody, comprising two heavy chains each comprising a heavy chain variable region ($V_H$), and two light chains each comprising a light chain variable region ($V_L$), wherein the $V_H$ and $V_L$ form an antigen binding site that specifically binds to CD47; and (b) a second antigen binding portion comprising two anti-TIGIT single domain antibodies, wherein the first antigen binding portion and the second antigen binding portion are fused to each other;

wherein the $V_H$ comprises heavy chain complementarity determining regions HCDR1, HCDR2, and HCDR3, and the amino acid sequences of the HCDR1, HCDR2, and HCDR3 are as shown in SEQ ID NO:31, SEQ ID NO:32 and SEQ ID NO:33, respectively; and the $V_L$ comprises light chain complementarity determining regions LCDR1, LCDR2 and LCDR3, and the amino acid sequences of the LCDR1, LCDR2, and LCDR3 are as shown in SEQ ID NO:34, SEQ ID NO:35 and SEQ ID NO:36, respectively;

wherein the two anti-TIGIT single domain antibodies each comprise complementarity determining regions CDR1, CDR2, and CDR3, and the amino acid sequences of the CDR1, CDR2, and CDR3 are as shown in SEQ ID NO:39, SEQ ID NO:40, and SEQ ID NO:41, respectively; and wherein:

the N-termini of the two anti-TIGIT single domain antibodies are fused, respectively, to the C-termini of the two heavy chains of the anti-CD47 antibody to form two heavy chain fusion polypeptides, each comprising a sequence having at least 95% identity with an amino acid sequence shown in SEQ ID NO:8 or SEQ ID NO:12, and the two light chains of the anti-CD47 antibody each comprises a sequence having at least 95% identity with the amino acid sequence shown in SEQ ID NO:6;

the C-termini of the two anti-TIGIT single domain antibodies are fused, respectively, to the N-termini of the two heavy chains of the anti-CD47 antibody to form two heavy chain fusion polypeptides, each comprising a sequence having at least 95% identity with an amino acid sequence shown in SEQ ID NO:10 or SEQ ID NO:14, and the two light chains of the anti-CD47 antibody each comprises a sequence having at least 95% identity with the amino acid sequence shown in SEQ ID NO:6;

the N-termini of the two anti-TIGIT single domain antibodies are fused, respectively, to the C-termini of the two light chains of the anti-CD47 antibody to form two light chain fusion polypeptides, each comprising a sequence having at least 95% identity with an amino acid sequence shown in SEQ ID NO:16 or SEQ ID NO:20, and the two heavy chains of the anti-CD47 antibody each comprises a sequence having at least 95% identity with the amino acid sequence shown in SEQ ID NO:4; or the C-termini of the two anti-TIGIT single domain antibodies are fused, respectively, to the N-termini of the two light chains of the anti-CD47 antibody to form two light chain fusion polypeptides, each comprising a sequence having at least 95% identity with an amino acid sequence shown in SEQ ID NO:18 or SEQ ID NO:22, and the two heavy chains of the anti-CD47 antibody each comprises a sequence having at least 95% identity with the amino acid sequence shown in SEQ ID NO:4.

2. An isolated polynucleotide encoding the bispecific antigen binding protein according to claim 1.

3. A vector comprising the isolated polynucleotide according to claim 2.

4. A host cell comprising the isolated polynucleotide according to claim 2.

5. A method for producing isolated anti-CD47/anti-TIGIT bispecific antigen binding protein, comprising culturing the host cell according to claim 4 under suitable conditions, and recovering antibody or fragments thereof from cells or cell culture fluid.

6. A pharmaceutical composition comprising the bispecific antigen binding protein according to claim 1 and a pharmaceutically acceptable carrier.

\* \* \* \* \*